(12) United States Patent
Heikkinen et al.

(10) Patent No.: US 12,383,153 B2
(45) Date of Patent: Aug. 12, 2025

(54) LOW POWER OPTICAL MEASUREMENTS

(71) Applicant: Oura Health Oy, Oulu (FI)

(72) Inventors: Olli Petteri Heikkinen, Oulu (FI);
Mika Petteri Kangas, Oulu (FI);
Jaakko Tapio Vartiainen, Oulu (FI);
Kirsi Marja Maansaari, Oulu (FI);
Jukka Tapani Mäkinen, Oulu (FI)

(73) Assignee: Oura Health Oy, Oulu (FI)

( * ) Notice: Subject to any disclaimer, the term of this patent is extended or adjusted under 35 U.S.C. 154(b) by 83 days.

(21) Appl. No.: 18/331,579

(22) Filed: Jun. 8, 2023

(65) Prior Publication Data

US 2024/0407657 A1    Dec. 12, 2024

(51) Int. Cl.
*A61B 5/024*    (2006.01)

(52) U.S. Cl.
CPC ...... *A61B 5/02416* (2013.01); *A61B 5/02438* (2013.01)

(58) Field of Classification Search
CPC . A61B 5/02416; A61B 5/02438; G01J 1/4204
See application file for complete search history.

(56) References Cited

U.S. PATENT DOCUMENTS

2014/0278229 A1*    9/2014    Hong ............... H04W 4/027
702/160

\* cited by examiner

*Primary Examiner* — Boniface N Nganga
(74) *Attorney, Agent, or Firm* — Holland & Hart LLP

(57) ABSTRACT

Methods, systems, and devices for adjusting a power output level of a light source on a wearable device are described. A photodetector on the wearable device may measure a first photoplethysmography (PPG) signal derived from an ambient light source that is powered externally to the wearable device. The wearable device may calculate a quality metric of the first PPG signal based on measuring the first PPG signal. The wearable device may adjust the power output level of the light source powered by the wearable device based on the quality metric of the first PPG signal.

20 Claims, 11 Drawing Sheets

LOW POWER OPTICAL MEASUREMENTS

FIELD OF TECHNOLOGY

The following relates to wearable devices and data processing, including low power optical measurements.

BACKGROUND

Some wearable devices may be configured to collect physiological data from users, including heart rate, motion data, temperature data, photoplethysmogram (PPG) data, and the like. In some cases, some wearable devices may include light sources that operate at constant power levels regardless of the quality of the physiological data signals, thereby reducing the overall battery life of the wearable device.

DETAILED DESCRIPTION

Figure 1:
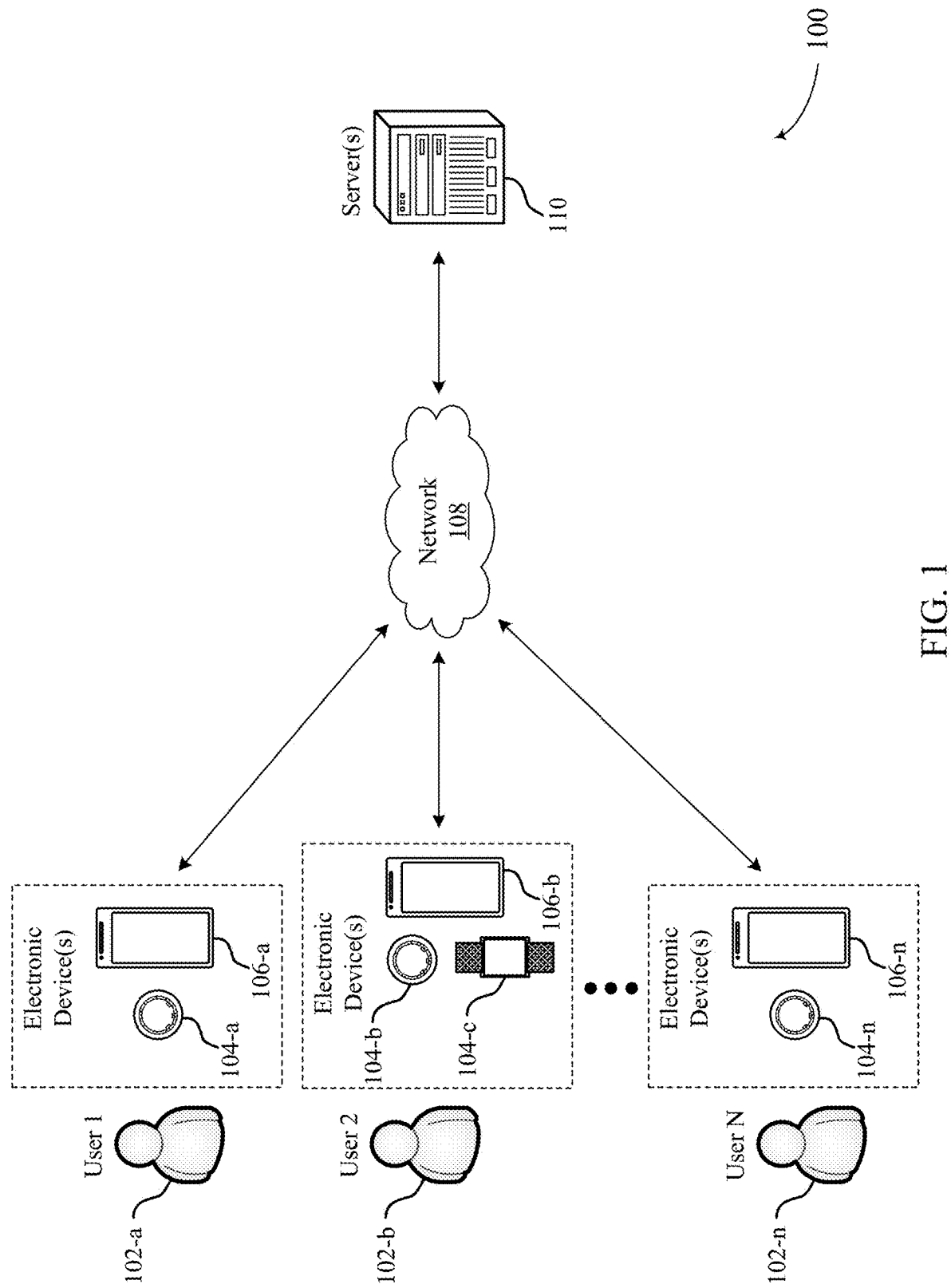
FIG. 1 illustrates an example of a system that supports low power optical measurements in accordance with aspects of the present disclosure.

Some wearable devices may be configured to collect physiological data from users, including photoplethysmogram (PPG) signals. In order to efficiently and accurately track physiological data, a wearable device may be configured to collect data continuously while the user wears the device. The wearable device may use the light propagation that travels from one or more light emitting diodes (LED), through the tissue, and to the photodetectors (PDs) for physiological measurements such as the PPG measurements. In such cases, the wearable device may use light emitted from a light source powered within the wearable device to measure physiological data signals. The light sources of a wearable device (e.g., LEDs or the like) may be configured to operate at relatively high and constant power levels regardless of the quality of the PPG signals or the presence of alternative or supplemental light sources. As such, the battery performance may suffer, which may reduce the overall operating battery life.

Conventional wearable devices have been unable to efficiently, accurately, and reliably perform measurements using light sources outside of the wearable device for a variety of reasons. For example, alternative light sources other than the LEDs of the sensor, may create new optical interfaces that couple light into the tissue of the user from uncontrolled positions and with uncontrolled intensity. The new optical interfaces may behave differently as compared to cases where there is a controlled contact between the skin of the user and the LEDs allowing control over the light input to the skin of the user and over an optical measurement path through intended physiological structures. In such cases, the new optical interfaces may change a critical angle due to reflections, reduce perfusion index due to internal stray light, cause variations in distribution of light, and the like. The variation in optical interface and variation in wavelength may cause inaccurate readings from an alternative, external light source, which may result in inaccurate measurements.

In some cases, the wearable device may be unable to efficiently and dynamically adjust a power of the LEDs, such as increasing or decreasing the brightness of an LED, to account for the variation in readings, which may increase power consumption at the wearable device. Taken together, these issues with wearable devices may result in inaccurate physiological data readings, which may lead to a distorted picture of the user's overall health (e.g., distorted PPG measurements), as well as increased power consumption and decreased battery life.

Accordingly, techniques described herein are directed to systems and methods for dynamically adjusting the power output of the LEDs based on real-time signal quality metrics. More specifically, aspects of the present disclosure are directed to techniques for operating the LEDs at lower power levels (or completely turning the LEDs off) by using ambient light as an additional or alternative light source as compared to using only LEDs (or other light sources within the wearable device). The wearable device may use ambient light external from the wearable device (e.g., sunlight, indoor fluorescent lights, etc.) as a signal source to capture PPG signals or as an additional source to allow lowering the power outputted by the LEDs. In some cases, using ambient light external from the wearable device as the signal source to capture PPG signals may maximize the PD signals.

The wearable device may determine the quality of the signal (e.g., the PPG signal) that is derived from the ambient light and determine whether to deactivate the LEDs and use the ambient light as the single light source or, alternatively, to operate the LEDs at a lower power level and refrain from using the ambient light as a light source. By dynamically adjusting the power output of the LEDs based on real-time signal quality metrics, techniques described herein may perform the same physiological measurements while consuming less power, which may lead to more accurate measurements. In such cases, utilizing ambient light as an external light source and optimizing the LED power based on one or more quality metrics may decrease a power consumption at the wearable device, which may lead to longer battery life.

The wearable device may perform a PPG measurement using a baseline power output of LEDs and perform a PPG measurement using ambient light. The wearable device may determine the quality of the signal measured with ambient light and adjust the power of the LEDs based on the quality of the signal. As described herein, the wearable device may adjust a power output level of a light source on the wearable device (e.g., the LED or vertical cavity surface-emitting laser (VCSEL)). The PD on the wearable device may measure a PPG signal derived from an ambient light source that is powered externally to the wearable device. The wearable device may calculate a quality metric of the PPG signal after measuring the PPG signal. In some cases, the wearable device may adjust the power output level of the light source powered by the wearable device based on the quality metric of the PPG signal to optimize the battery life of the wearable device.

Aspects of the disclosure are initially described in the context of systems supporting physiological data collection from users via wearable devices. Aspects are then described in the context of wearable device diagrams, a process flow, and timing diagrams. Aspects of the disclosure are further illustrated by and described with reference to apparatus diagrams, system diagrams, and flowcharts that relate to low power optical measurements.

FIG. 1 illustrates an example of a system 100 that supports low power optical measurements in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.gVC-SELs, and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules: 4) weekly rhythms, or other artificial time periodicities exogenously imposed (e.g. in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for measuring a PPG signal using ambient light and adjusting the power output of the LEDs based on the quality of the PPG signal. For example, the system 100 may measure, at the PD on the wearable device 104, a PPG signal derived from an ambient light source that is powered externally to the wearable device 104 (e.g., sunlight, fluorescent lights, and the like). In such cases, the system 100 may calculate a quality metric of the PPG signal derived from the ambient light source that is powered externally to the wearable device 104 in response to measuring the PPG signal derived from the ambient light source.

The system 100 may adjust the power output level of the light source powered by the wearable device 104 based on the quality metric of the PPG signal derived from the ambient light source. For example, the system 100 may deactivate (e.g., turn off) the LED or decrease the power output level of the LED while keeping the LED activated (e.g., turned on). In such cases, the system 100 may use ambient light as an external light source and optimize the LED power, thereby decreasing the power consumption at the wearable device 104 and increasing the battery life of the wearable device 104.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
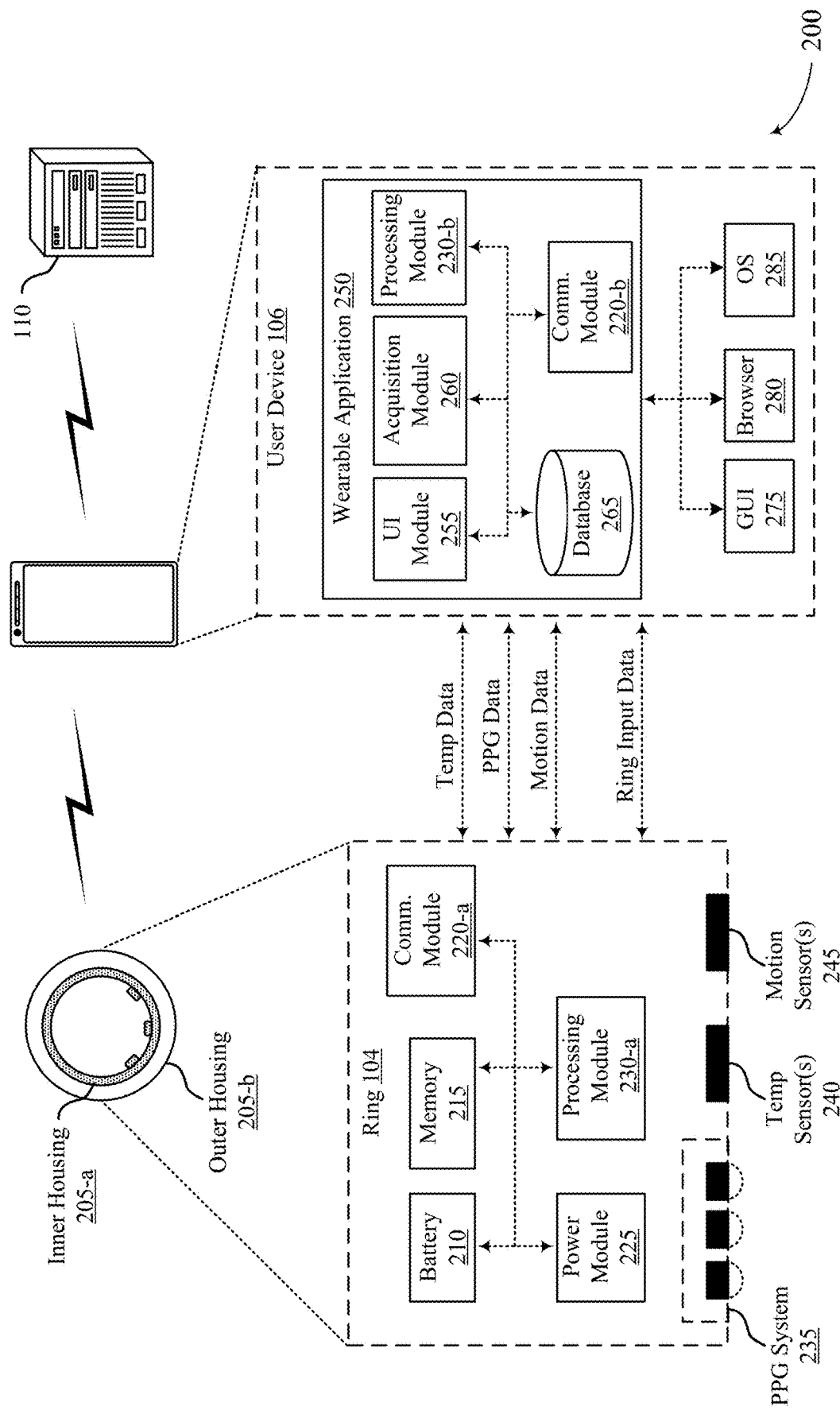
FIG. 2 illustrates an example of a system that supports low power optical measurements in accordance with aspects of the present disclosure.

FIG. 2 illustrates an example of a system 200 that supports low power optical measurements in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated.

In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support a wearable device that adjusts a power output level of a light source on the wearable device 104. In particular, techniques described herein support a ring 104, such as a wearable device 104 as described with reference to FIG. 1. For example, a ring 104 may include an inner housing 205-a configured to house a sensor module that includes one or more sensors that are configured to acquire physiological data from a user 102. The one or more sensors of the ring 104 may obtain physiological measurements from the user (e.g., temperature sensors, additional LED-PD sensors used for measuring heart rate, oxygen saturation, one or more sensors that a device may use to detect whether a user is asleep, or the like).

In some cases, the one or more sensors of the ring 104 are configured to acquire the physiological data from the user based on arterial blood flow, temperature, etc. In some implementations, the one or more sensors of the ring 104 are configured to acquire the physiological data (e.g., including PPG data) from the user based on blood flow that is diffused into the microvascular bed of skin with capillaries and arterioles. The one or more sensors of the ring 104 may be an example of PDs from the PPG system 235, temperature sensors 240, motion sensors 245, and other sensors.

As described herein, the wearable device of the system 200 may measure, at the PD, a PPG signal derived from an ambient light source that is powered externally to the wearable device (e.g., an alternative light source other than the LED). The system 200 may calculate a quality metric of the PPG signal after measuring the PPG signal. In such cases, the system 200 may adjust the power output level of the LED based on the quality metric of the PPG signal.

While much of the present disclosure describes one or more components in the context of a wearable ring device, aspects of the present disclosure may additionally or alternatively be implemented in the context of other wearable devices. For example, in some implementations, the one or more components described herein may be implemented in the context of other wearable devices, such as bracelets, watches, necklaces, piercings, and the like. For example, the wearable device 104 may surround a finger, wrist, ankle, earlobe, or the like of a user.

As noted previously herein, the ring 104 of the system 200 may be worn by a user to collect data from the user, including temperature data, sleep data, recovery data, activity data, heart rate data, HRV data, respiratory data, breathing rate data, blood pressure data, blood glucose data, and the like. The ring 104 of the system 200 may collect the physiological data from the user based on temperature sensors and measurements extracted from arterial blood flow (e.g., using PPG signals). In some cases, the ring 104 may collect the physiological data from the user based on measurements extracted from capillary blood flow, arteriole blood flow, or both. The physiological data may be collected continuously.

In some implementations, the one or more sensors of the ring 104 may sample the user's temperature continuously throughout the day and night. Sampling at a sufficient rate (e.g., one sample per minute) throughout the day and/or night may provide sufficient temperature data for analysis described herein. In some implementations, the ring 104 may continuously acquire temperature data (e.g., at a sampling rate). In some examples, even though temperature is collected continuously, the system 200 may leverage other information about the user that it has collected or otherwise derived (e.g., sleep stage, activity levels, illness onset, etc.) to select a representative temperature for a particular day that is an accurate representation of the underlying physiological phenomenon.

Figure 3:
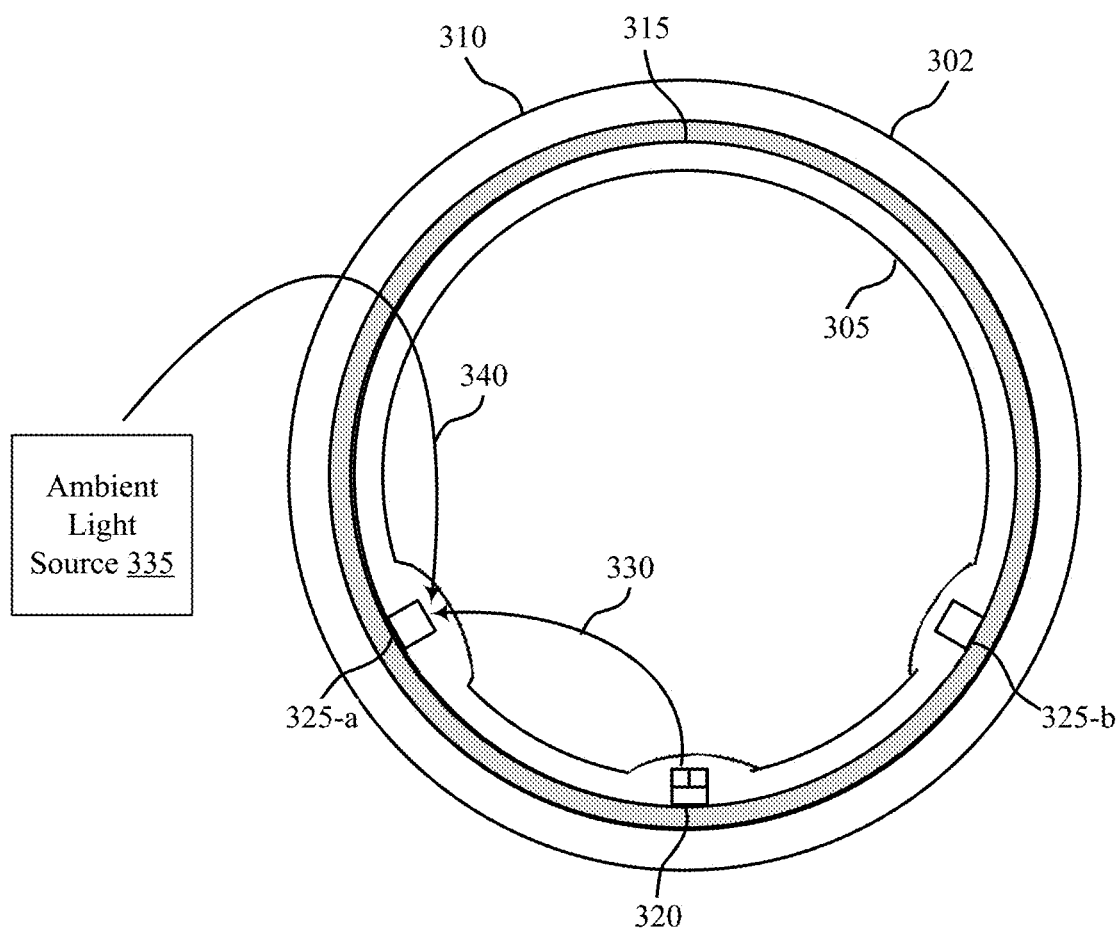
FIG. 3 shows an example of a wearable device diagram that supports low power optical measurements in accordance with aspects of the present disclosure.

FIG. 3 shows an example of a wearable device diagram 300 that supports low power optical measurements in accordance with aspects of the present disclosure. The wearable device diagram 300 may implement, or be implemented by, aspects of the system 100, system 200, or both. For example, the wearable device diagram 300 may include a wearable device 302 that may illustrate an example of a wearable device 104 as described with reference to FIG. 1. Although the wearable device 302 is illustrated as a ring in FIG. 3, the wearable device 302 may be any example of any wearable device (e.g., a watch, a necklace, and the like).

In some examples, the wearable device 302 may include an inner housing 305 and an outer housing 310, which may be examples of an inner housing 205 and outer housing 205-b as described with reference to FIG. 2. One or more sensors may be embedded in the inner housing 305, such as one or more LEDs 320 for collecting physiological measurements. In some cases, an outer opaque shell may be molded over an inner structure of the wearable device 302.

The wearable device 302 may be an example of a wearable ring device. For example, the PPG signals acquired along the respective channels illustrated in the wearable device diagram 300 may be acquired as a combination of the transmissive and reflective light transmitted through the skin of the finger. In such cases, the system may measure PPG measurements at different locations of the finger by transmitting or reflecting the light through a portion of the finger (e.g., widest portion of the finger) where the smaller arteries (e.g., arterioles) are located. Comparatively, other portions of the body (e.g., top of the wrist) may not include arterioles and may include bone and other bodily material which may interfere with physiological measurements collected by some wearable devices. As such, some other wearable devices, such as wearable devices worn around the wrist, may be unable to acquire physiological data based on blood flow within arterioles, which may result in inferior physiological measurements as compared to measurements acquired using a wearable ring device, thereby decreasing an efficiency and reliability of acquired physiological measurements.

The wearable device 302 in wearable device diagram 300 may include an electronic substrate 315, such as a printed wiring board (PWB) or PCB. The PCB may have both flexible and rigid sections. One or more sensors may be embedded in the electronic substrate 315. For example, the electronic substrate may include one or more LEDs 320 and PDs 325. The wearable device 302 may include LED 320, which may emit light 330 received by PD 325-a and/or PD 325-b. In this regard, the LED 320 may support an optical channel for physiological data measurements. For example, the optical channel may be between the LED 320 and the PD 325-a.

The wearable device 302 may include any number of LEDs, PDs, and respective optical channels for physiological data measurements. In some cases, LED 320 may be a red LED, a green LED, an infrared LED, a blue LED, or a laser diode which may emit light 330 that is scattered and absorbed by the skin of a user of the wearable device diagram 300 (e.g., reflective and/or transmissive measurements). In some cases, each of the LED 320, PD 325-a, and PD 325-b may be positioned at different radial positions relative to an axis of the wearable device 302 and along an inner circumference of the wearable device 302. In some examples, the PD 325-a may be positioned at a radial position opposite of the PD 325-b. The PPG signal from a green LED (e.g., LED 320) may include a stronger signal as compared to a PPG signal from an infrared LED (e.g., LED 320).

In some cases, the inner housing 305 may include a dome structure over the one or more LEDs 320, one or more PDs 325, or both. For example, the wearable device 302 may include dome structures over LED 320, PD 325-a, and PD 325-b to improve contact with the skin. In some other cases, there may be a window for the LED 320 to emit light 330. An optical interface may form between the inner housing 305 and the domes or the windows (e.g., with a refractive index of ~1.57) and the top layer of skin (e.g., with a refractive index of ~1.55). The wearable device 302 may use the light propagation from the LEDs 320 to the PDs 325 through tissue for physiological measurements, such as PPG and SpO2 measurements. That is, the wearable device 302 may use light 330 from LED 320 to measure SpO2 or PPG.

The wearable device diagram 300 may include an ambient light source 335, which may emit light 340 received by PD 325-a and/or PD 325-b. In this regard, the ambient light source 335 may support an optical channel for physiological data measurements. For example, the optical channel may be between the ambient light source 335 and the PD 325-a. In some cases, ambient light source 335 may be an example of a light source powered externally from the wearable device 302. For example, the ambient light source 335 may be an example of fluorescent lights, sunlight, and the like. The ambient light source 335 may emit light 340 that is scattered and absorbed by skin of a user of the wearable device 302 (e.g., reflective and/or transmissive measurements). In some cases, the wearable device 302 may use light 340 from ambient light source 335 to measure SpO2 or PPG. Light 340 may penetrate the skin to a different depth than light 330 due to the varying wavelengths.

In such cases, the system may measure the two different lights via a same PD 325-a which may increase the diversity of the measurement in addition to measuring PPG measurements using two different light sources. That is, the wearable device diagram 300 may include a 2:1 relationship between the light sources (e.g., LED 320 and ambient light source 335) and the PD 325-a. In some aspects, separate PPG signals may be acquired along each of the respective optical channels. Moreover, in some implementations, the LED 320 may be configured to generate light 330 with a different wavelength as compared to the light 340 generated by the ambient light source 335, which may further improve a diversity of measurements (e.g., PPG signals) acquired within the wearable device diagram 300.

In some implementations, a single PD 325 may be used together with multiple light sources (e.g., ambient light source 335 and LED 320) to save cost and space. By measuring the signals (e.g., at PDs 325), it may be possible to use LED 320 and PD 325 pairs and ambient light source 335 and PD 325 pairs that have sufficient optical paths during rapid motion and reduce battery consumption. However, the system may adjust a power level output by the LED 320 to utilize the ambient light source 335 thereby reducing the overall power consumption of the wearable device 302. For example, using the ambient light source 335 may decrease the power consumption and increase the battery life of the wearable device 302.

The system may measure, at the PD 325-a, a PPG signal derived from the LED 320. The PPG signal may be an example of an initial measurement of PPG to use as a baseline power output level of the LED 320. The system may measure, at the PD 325-a, a PPG signal derived from the ambient light source 335. The system may calculate a quality metric of the PPG signal derived from the ambient light source 335 to determine whether to adjust the power output level of the LED 320. In such cases, the system may perform a quality assessment of the PPG signal derived from the ambient light source 335 as compared to the PPG signal derived from the LED 320.

The system may determine that the quality assessment of the PPG signal derived from the ambient light source 335 satisfies a threshold. In such cases, the system may adjust the power output level of the LED 320 by turning down the power output level of the LED 320 or turning off the power output level of the LED 320 altogether. For example, the system may use the ambient light source 335 to power the PPG measurements as a single light source or in addition to the LED 320. The ambient light source 335 may be used as a signal source to capture the PPG measurements while optimizing the power output of the LED 320 based on the quality metric of the PPG signal derived from the ambient light source 335.

The system may calculate the quality metric of the PPG signal derived from the ambient light source 335 and determine to use the ambient light source 335 for the PPG measurements. For example, the system may use the ambient light source 335 in an office environment (e.g., with fluorescent ceiling lights as the ambient light source 335), outside on a bright, sunny day, or both. The system may decrease the power output of the LED 320 (e.g., a green LED) in cases where the ambient light source 335 is used. The light 340 may include a narrow spectrum of wavelengths in the presence of fluorescent lights as the ambient light source 335 or a wide spectrum of wavelengths in the presence of natural sunlight as the ambient light source 335.

Regardless of the wavelengths, the light 340 may penetrate the skin in several positions around the wearable device 302 such that the system may measure PPG measurements at different locations of the finger. In some cases, the LEDs 320 may use a range of 3 to 10 milliamps (mA) to perform the PPG measurements. However, utilizing the ambient light source 335 may enable the LEDs 320 to use less electrical current to perform PPG measurements. For example, the LEDs 320 may use a range of 0 to 0.5 mA to perform the same PPG measurement when utilizing the ambient light source 335. As described herein, a combined channel selection based on a spectrogram or time domain signaling may increase the accuracy of the signaling and decrease the overall power consumption of the wearable device 302.

The wavelengths of the light 340 from the ambient light source 335 may be unknown to the system. In such cases, the system may calculate the quality metric of the PPG signal from the ambient light source 335 in order to determine whether to use the ambient light source 335, the LED 320, or both. In some cases, the light 340 from the ambient light source 335 may include a heart rate signal derived from the PPG signal. For example, the PPG signal may satisfy the threshold and include the heart rate signal based on satisfying the threshold. In some cases, an ambient light cancellation technique may remove the heart rate information from the PPG signal. For example, the heart rate information may be removed from the PPG signal based on the intensity of the LED 320 being lower than an intensity of the ambient light source 335. In such cases, the system may remove heart rate information from the PPG measurement if the ambient light source 335 results in a stronger PPG signal than the LED 320.

The ambient light cancellation technique may be disabled to prevent the heart rate information from being removed from the PPG signal. In such cases, the ambient light cancellation technique may be dynamically turned on and off based on the quality metric of the PPG signal derived from the ambient light source 335. The ambient light cancellation technique may record the PD 325-*a* input of light received before and after the LED 320 illuminates. In such cases, the PD 325-*a* may measure the light 330 and the light 340 before, during, and after the LED 320 illuminates regardless of whether the ambient light cancellation technique is used. By deactivating the ambient light cancellation technique when the ambient light source 335 is used, the system may save additional power consumed by the wearable device 302. Comparing the PPG signal from the LED 320 and the PPG signal from the ambient light source 335 may determine whether the system uses the ambient light source 335 and deactivates the ambient light cancellation technique.

In dark environments (e.g., environments without sunlight, fluorescent lights, and the like), the ambient light cancellation technique may be dynamically adjusted to be deactivated, thereby decreasing the power consumption of the wearable device 302. That is, in dark environments, the ambient light may not be cancelled, so the ambient light cancellation technique may be turned off in order to save energy. For example, the system may determine that the PPG signal derived from the ambient light source 335 fails to satisfy the quality metric threshold, and the system may refrain from using the ambient light source 335. In such cases, the system may deactivate (e.g., turn off) the ambient light cancellation technique. The ambient light cancellation technique may be deactivated to prevent measuring the light 330 before and after the LED 320 is activated which may save processing power from activating the PD 325-*a*.

In some cases, the ambient light source 335 may not emit enough light 340 to be received at the PD 325-*a*. In such cases, the system may use the LED 320 to perform PPG measurements, and the ambient light cancellation technique may not be activated because the ambient light source 335 is not used. The LED 320 may operate at a reduced power output level such that a green LED 320 may use a low driving current. For example, previous wearable devices may use an LED operating at a range between 10 to 120 mA LED current. However, the wearable device 302 may now use an LED operating at 0.5 mA LED current to increase the efficiency of the overall wearable device 302.

In some examples, the system may remove certain physiological measurements to increase the quality of the PPG signals. For example, the system may detect longer wavelengths and remove measurements that include blood alcohol measurements to increase the quality of the PPG signals. In some cases, the ambient light source 335 may be used based on a time of day, motion associated with the user, a sleep position of the user, or a combination thereof. In some examples, the system may use the ambient light source 335 to measure daytime heart rate. For example, when a user exercises and the system measures the PPG signal, the strength of the light 340 may be greater than a strength of the light 330 from the LED 320. The system may measure a static metric of the light 340 and determine whether the light 340 experiences a change in frequency. The system may determine that that light 340 is static and use the ambient light source 335 to power the PPG measurements. In such cases, the system may refrain from activating the LEDs 320 when the user is exercising and the outdoor, natural sunlight is the ambient light source 335. In some cases, as described with reference to FIG. 4, the system may measure the light 340 from a light guide to determine whether the system may use the ambient light source 335.

Figure 4:
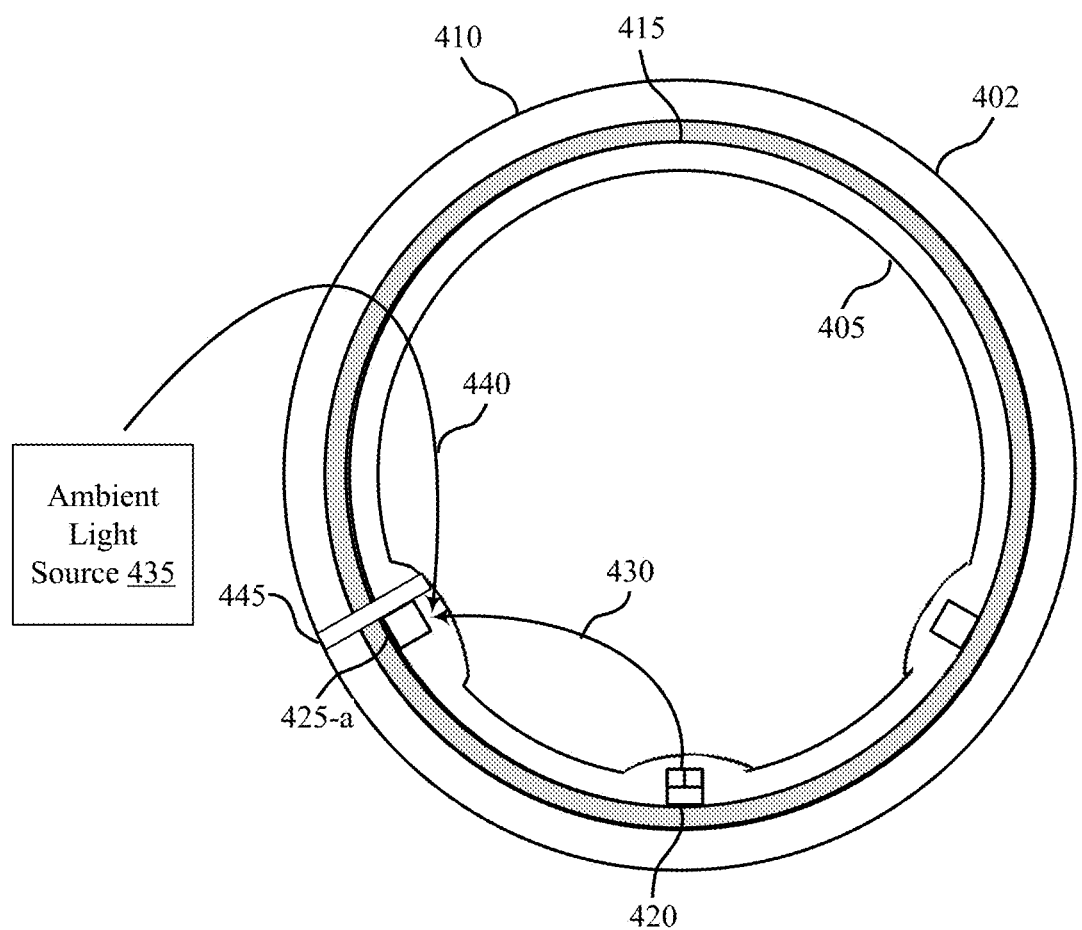
FIG. 4 shows an example of a wearable device diagram that supports low power optical measurements in accordance with aspects of the present disclosure.

FIG. 4 shows an example of a wearable device diagram 400 that supports low power optical measurements in accordance with aspects of the present disclosure. The wearable device diagram 400 may implement, or be implemented by, aspects of the system 100, system 200, or both. For example, the wearable device diagram 400 may include a wearable device 402 that may illustrate an example of a wearable device 104 as described with reference to FIG. 1. Although the wearable device 402 is illustrated as a ring in FIG. 4, the wearable device 402 may be any example of a wearable device (e.g., a watch or bracelet, a necklace, and the like).

The wearable device 402 may include a light guide 445. The light guide 445 may extend from the outer housing 410 to the inner housing 405. In such cases, the light guide 445 may extend from an external surface of the wearable device 402 to an inner surface of the wearable device 402. The light guide 445 may be an example of a channel or a window that directs light 430, light 440, or both into the tissue of the user, the PD 425-*a*, or both. The light guide 445 may include a clear, epoxy material. In some cases, the light guide 445 may be an example of a window or a pipe with TIR. For example, the light guide 445 may include a mirrored surface, a prism of various shapes, and the like. In such cases, the light guide 445 may collect light 430 and light 440 into the wearable device 402.

The light guide 445 may comprise a material that transmits and/or funnels light 430 from the LED 420 to the PD 425-*a*, light 440 from the ambient light source 435, or both. In some cases, the light guide 445 may be positioned adjacent to the PD 425-*a* to direct light 440, light 430, or both into the PD 425-*a*. In other examples, a light guide 445 may be positioned adjacent to the LED 420, the PD 425-*b*, or both. The wearable device 402 may include one or more light guides 445. For example, the PD 425-*a* may include a light guide 445 positioned on either side of the PD 425-*a*. In some cases, the outer cover 410 may include a channel (e.g., a groove throughout the material of the outer cover 410) that guides the light from outside of the wearable device 402 and into the wearable device 402.

In some cases, a light guide sensor (e.g., a PD) may be attached to the light guide 445 such that the light guide sensor may measure an amount of light 440 received at the PD 425-*a* and measure an amount of light 430 received at the PD 425-*a*. In such cases, the light guide sensor may compare the amount of light 440 to an amount of light 430 received at the PD 425-*a*. In some cases, the light guide sensor may signal, to the wearable device 302, to deactivate the LED 420 based on an amount of light 440 received from the ambient light source 435. In other examples, the light guide sensor may signal, to the wearable device 402, to deactivate the LED 420 or lower the power output level of the LED 420 based on a quality metric of the PPG signal derived from the ambient light source 435. For example, the light guide sensor may measure an amount of light 440 coming into the light guide 445 and determine that an amount of light 440 received at the PD 425-*a* and a quality of light 440 satisfies a threshold to use the ambient light source 435 as opposed to the LED 420 or in addition to the LED 420, thereby reducing the power consumption of the LED 420.

In some cases, the wearable device 402 may include a filter disposed over the PD 425-a. For example, the filter may be an example of a film disposed on top of the dome over the PD 425-a. Because the ambient light source 435 may emit a wide spectrum of light 440, the light 440 may be filtered to omit the noise from the PPG signal. In such cases, the PPG signal may include less noise after the light 440 travels through the filter disposed over the PD 425-a. In some cases, an amount of light may be filtered on the detector side (e.g., PD 425-a), the source side (e.g., LED 420, ambient light source 435), or both. In some cases, spectral filtering may be used in addition to light guide filtering via light guide 445. The filter may be an example of an absorption filter that includes a transmission window with a filter for certain wavelengths. In some cases, the sensors may include a filter on the pixels of the sensors. In such cases, a pixelated sensor may be used for different wavelengths, different spectrum peaks, different spectrum windows, or a combination thereof.

In some cases, the wearable device 402 may store light 440 for future use. The light 440 may be stored within the wearable device 402. For example, the light 440 may be stored within the light guide 445. In some cases, the light 440 may be stored and released at a later time as a PPG sensor source. The wearable device 402, including at least the PD 425-a, the light guide 445, or both, may use a phosphorescent material that stores the light 440 and releases the light 440 to the PD 425-a after a duration of time expires based on the material properties of the phosphorescent material. In some cases, an electrically activated component (e.g., a liquid crystal shutter) may release the light 440 to the PD 425-a after the wearable device 402 determines that the signal derived from the LED 420 fails to satisfy a threshold. For example, the phosphorescent material may store the light 440, and the electrically activated component may release the light 440 to disable the LED 420 and conserve power of the wearable device 402. In some examples, the phosphorescent material of the wearable device 402 may store the light 440, and the electrically activated component may release the light 440 during the night such that the LED 420 may be deactivated. In such cases, the wearable device 402 may optically gather light 440 to determine the optimal timing to use the light 440 via the light guide 445, a filter on the sensors, or both.

Figure 5:
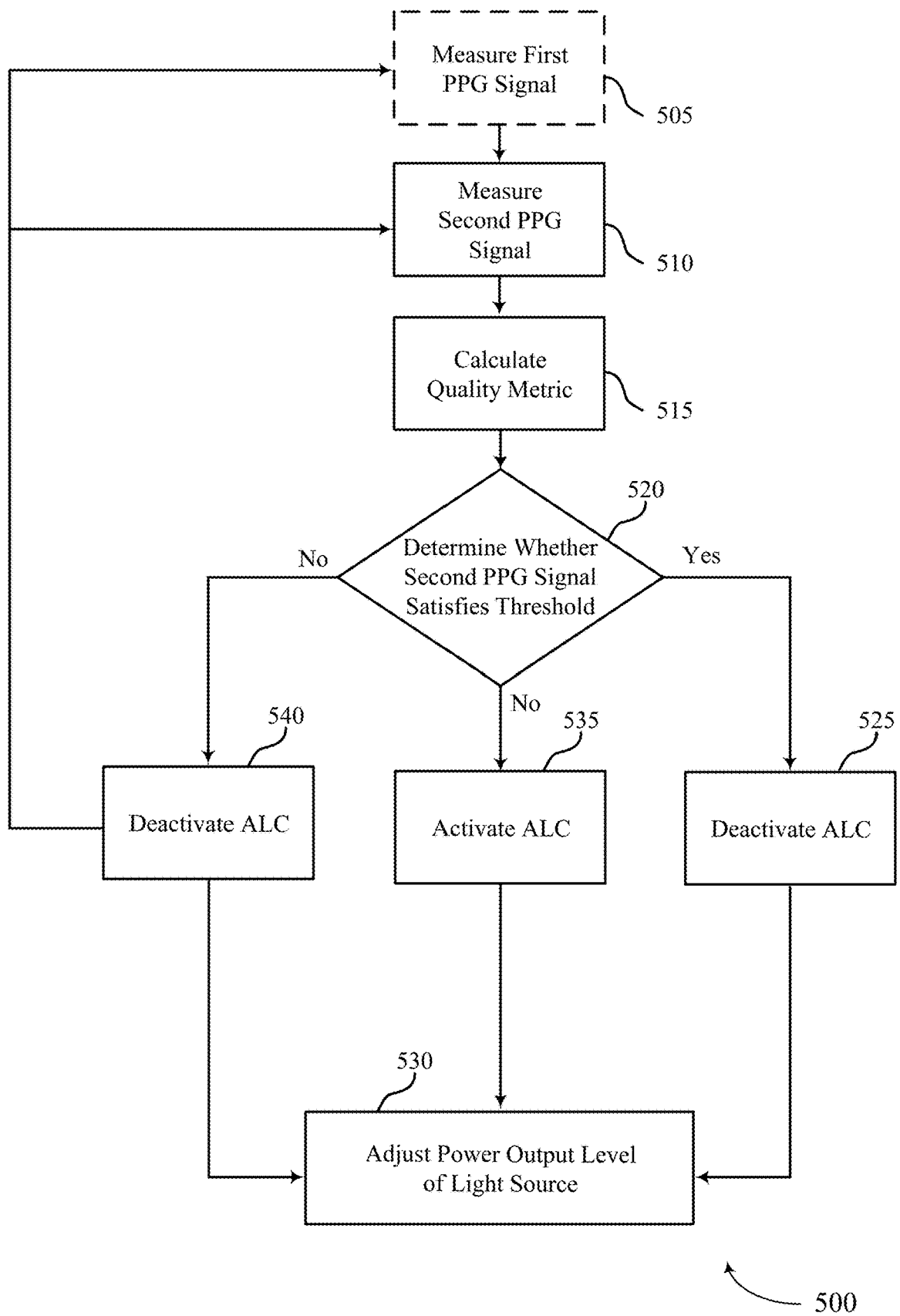
FIG. 5 shows an example of a process flow that supports low power optical measurements in accordance with aspects of the present disclosure.

FIG. 5 shows an example of a process flow 500 that supports low power optical measurements in accordance with aspects of the present disclosure. The process flow 500 may be implemented by the system 100 and system 200 including at least a server 110, a user device 106, a wearable device 104, or some combination of components from these devices The process flow 500 may be implemented by the wearable device diagram 300, wearable device diagram 400, or both. Alternative examples of the following may be implemented, where some steps are performed in a different order than described or not performed at all. In some cases, steps may include additional features not mentioned below, or further steps may be added.

Much of the present disclosure may be described in the context of a first PPG signal and a second PPG signal. Accordingly, the terms "first," "second," and like terms, may be used interchangeably, unless noted otherwise herein, as the terms "first" and "second" may be used to differentiate between two signals derived from two different light sources. However, the use of the terms "first" and "second" are not to be regarded as limiting, as it is contemplated herein that aspects of the present disclosure may measure two different signals derived from two different light sources.

In some cases, at 505, the wearable device may measure a first PPG signal. For example, a PD on the wearable device may measure a first PPG signal derived from the light source powered by the wearable device. The light source powered by the wearable device may be an example of an LED. For example, the first PPG signal may be acquired using the LED and one or more PDs. In some cases, receiving the first PPG signal may be based on the motion data satisfying a threshold motion metric, the temperature data satisfying a threshold temperature metric, or both. In some examples, the system may receive the first PPG signal based on the heart rate satisfying a threshold heart rate metric, the PPG signal feature data satisfying a threshold metric, or both. The received first PPG signal may be saved to a local memory storage. As described herein, the wearable device may determine whether to use the ambient light source as a single source based on the quality of the measurement derived from the ambient light source, regardless of measuring the first PPG signal derived from the light source powered by the wearable device.

At 510, the wearable device may measure a second PPG signal. For example, the PD on the wearable device may measure the second PPG signal. The second PPG signal may be derived from an ambient light source that is powered externally to the wearable device. In some cases, the wearable device may measure the second PPG signal before measuring the first PPG signal, after measuring the first PPG signal, or at a same time as measuring the first PPG signal.

For example, the second PPG signal may be acquired using the ambient light source and one or more PDs. In some cases, receiving the second PPG signal may be based on the motion data satisfying a threshold motion metric, the temperature data satisfying a threshold temperature metric, or both. In some examples, the system may receive the second PPG signal based on the heart rate satisfying a threshold heart rate metric, the PPG signal feature data satisfying a threshold metric, or both. The received second PPG signal may be saved to a local memory storage.

At 515, the wearable device may calculate a quality metric. For example, the wearable device may calculate the quality metric of the second PPG signal based on measuring the second PPG signal. The wearable device may compare a morphology of the first PPG signal and a morphology of the second PPG signal in response to measuring the second PPG signal and measuring the first PPG signal. In such cases, the wearable device may compare the morphology of the first PPG signal and the morphology of the second PPG signal to calculate the quality metric of the second PPG signal. As such, the wearable device may compare the morphology of the signal derived from ambient light to the signal derived from LEDs.

The morphology of the first PPG signal and the morphology of the second PPG signal may each include a pulse amplitude, a systolic gradient, a signal to noise ratio, or a combination thereof, as described with reference to FIG. 6. For example, the wearable device may calculate the pulse amplitude of the second PPG signal in response to measuring the second PPG signal. The wearable device may calculate the quality metric of the second PPG signal based on calculating the pulse amplitude of the second PPG signal. In such cases, the wearable device may determine the quality metric of the pulse amplitude to determine whether to use the ambient light, the LEDs, or both as the light source to measure the PPG signal.

In some cases, the wearable device may calculate a signal to noise ratio of the second PPG signal in response to measuring the second PPG signal. The wearable device may calculate the quality metric of the second PPG signal based on calculating the signal to noise ratio of the second PPG signal. In such cases, the wearable device may determine the quality metric of the signal to noise ratio to determine whether to use the ambient light, the LEDs, or both as the light source to measure the PPG signal.

In some examples, the wearable device may calculate a systolic gradient of the second PPG signal after measuring the second PPG signal. The wearable device may calculate the quality metric of the second PPG signal based on calculating the systolic gradient of the second PPG signal. In such cases, the wearable device may determine the quality metric of the systolic gradient to determine whether to use the light source of ambient light, the LEDs, or both.

The wearable device may calculate the quality metric of the first PPG signal based on measuring the first PPG signal. The wearable device may compare the morphology of the first PPG signal and the morphology of the second PPG signal to calculate the quality metric of the first PPG signal. In some cases, the wearable device may calculate the pulse amplitude of the first PPG signal in response to measuring the first PPG signal. The wearable device may calculate the quality metric of the first PPG signal based on calculating the pulse amplitude of the first PPG signal. In some cases, the wearable device may calculate a signal to noise ratio of the first PPG signal in response to measuring the first PPG signal. The wearable device may calculate the quality metric of the first PPG signal based on calculating the signal to noise ratio of the first PPG signal. In some examples, the wearable device may calculate a systolic gradient of the first PPG signal after measuring the first PPG signal. The wearable device may calculate the quality metric of the first PPG signal based on calculating the systolic gradient of the first PPG signal.

At 520, the wearable device may determine whether the quality metric of the second PPG signal satisfies a threshold based on calculating the quality metric of the second PPG signal. In some cases, the wearable device may determine whether the quality metric of the first PPG signal satisfies a threshold based on calculating the quality metric of the first PPG signal.

At 525, the wearable device may determine that the quality metric of the second PPG signal satisfies a threshold in response to calculating the quality metric of the second PPG signal. For example, the wearable device may deactivate an ambient light cancellation technique based on determining that the quality metric of the second PPG signal satisfies the threshold. In such cases, the wearable device may determine that the signal measured with ambient light (e.g., the second PPG signal) has a higher quality than the signal measured with the LED (e.g., the first PPG signal). For example, the PPG signal quality with ambient light may be adequate (e.g., satisfy the threshold), and the ambient light cancellation technique may be deactivated such that the ambient light may be used alone for measurements or together with LEDs in sensor measurements.

The wearable device may disable (e.g., turn off) the ambient light cancellation technique after determining that the signal measured using ambient (e.g., the second PPG signal) has a higher quality metric than the signal measured using the LEDs (e.g., the first PPG signal). For example, the wearable device may determine that ambient light includes adequate quality with respect to the calculated quality metrics threshold. In such cases, the wearable device may use ambient light as the light source in heart rate measurement. In some examples, the wearable device may determine that the quality metric of the second PPG signal satisfies a threshold during the day.

At 525, the wearable device may determine that the quality metric of the first PPG signal fails to satisfy a threshold in response to calculating the quality metric of the first PPG signal. For example, the wearable device may deactivate an ambient light cancellation technique based on determining that the quality metric of the first PPG signal fails to satisfy the threshold. Ambient light cancellation works by recording the PD input just before and after lighting up the LED, and then removing the ambient light input from the LED-illuminated data sample.

At 530, the wearable device may adjust the power output level of the light source powered by the wearable device. For example, the wearable device may deactivate the light source powered by the wearable device in response to determining that the quality metric of the second PPG signal satisfies the threshold. The wearable device may deactivate (e.g., turn off) the LEDs based on determining that the signal measured with ambient light is a better quality than the signal measured with the LED, that the ambient light includes adequate quality with respect to the calculated quality metrics, or both.

For example, the wearable device may adjust the power output level of the light source powered by the wearable device based on the quality metric of the second PPG signal. The wearable device may adjust the power output level of the light source powered by the wearable device based on determining that the quality metric of the second PPG signal satisfies the threshold, deactivating the ambient light cancellation technique, or both. The power output level of the light source powered by the wearable device may be adjusted to be less than a baseline power output level of the light source powered by the wearable device. The wearable device may perform the PPG measurement using a low power LED or without using the LED altogether.

In some cases, the power output level of the LED may be adjusted based on calculating the pulse amplitude of the second PPG signal, calculating the signal to noise ratio of the second PPG signal, calculating the systolic gradient of the second PPG signal, or a combination thereof. For example, the power output of the LED may be adjusted based on comparing the morphology of the first PPG signal and comparing the morphology of the second PPG signal. In some examples, the power output level of the LED may be adjusted based on deactivating the light source powered by the wearable device.

In some examples, the power output level of the LED may be adjusted based on calculating the pulse amplitude of the first PPG signal, calculating the signal to noise ratio of the first PPG signal, calculating the systolic gradient of the first PPG signal, or a combination thereof. In some examples, the power output level of the LED may be adjusted based on deactivating the ambient light cancellation technique.

At 535, the wearable device may determine that the quality metric associated with the second PPG signal fails to satisfy a threshold. For example, the wearable device may determine that the quality metric of the second PPG signal fails to satisfy the threshold in response to calculating the quality metric. In such cases, the wearable device may activate the ambient light cancellation technique in response to determining that the quality metric of the second PPG signal fails to satisfy the threshold. For example, some ambient light may be present, but the PPG signal quality measured with ambient light may be too low (e.g., fails to satisfy the threshold), and the ambient light cancellation technique may be activated as the LEDs are used for sensor measurements. The wearable device may determine that the signal measured with ambient light is worse quality than the signal measured with the LED. In such cases, the wearable device may enable (e.g., turn on) ambient light cancellation technique to cancel out the ambient light and use the LED to measure the PPG signal.

At 535, the wearable device may determine that the quality metric associated with the first PPG signal satisfies a threshold. For example, the wearable device may determine that the quality metric of the first PPG signal satisfies the threshold in response to calculating the quality metric of the first PPG signal. In such cases, the wearable device may activate the ambient light cancellation technique in response to determining that the quality metric of the first PPG signal satisfies the threshold.

At 530, the wearable device may adjust the power output level of the light source powered by the wearable device based on activating the ambient light cancellation technique. For example, the power output level of the light source powered by the wearable device may be adjusted to be less than a baseline power output level of the light source powered by the wearable device after determining that the quality metric of the second PPG signal fails to satisfy the threshold. In such cases, the wearable device may perform the PPG measurement using a low powered LED. The wearable device may adjust the power output of the LED in response to activating the ambient light cancellation technique. For example, a low powered green LED and a low powered IR LED may be utilized while the ambient light cancellation technique is turned on (e.g., cancelling out the ambient light).

At 540, the wearable device may determine that the quality metric associated with the second PPG signal fails to satisfy a threshold in response to calculating the quality metric of the second PPG signal. In such cases, the wearable device may determine that the quality metric associated with the second PPG signal (e.g. the ambient light level) is below the threshold. For example the wearable device may deactivate the ambient light cancellation technique in response to determining that the ambient light level (e.g., the quality metric of the second PPG signal) is below the threshold. The ambient light may not be cancelled because of the lack of ambient light present in dark environments, and the ambient light cancellation technique may be turned off (e.g., deactivated). In such cases, the wearable device may turn off the ambient light cancellation technique if there is no ambient light or a very low level of ambient light (e.g., during the night or in a dark day-time environment).

During the night, the wearable device may use a low driving current for green LEDs for heart rate measurements. The sleep heart rate measurements with low light green PPG may be more efficient than IR with very low power settings. The low power settings may be an example of 0.5 mA LED current. In some cases, the night-time heart rate using an IR LED may use a range of 10 to 120 mA LED current. In the dark, the ambient light cancellation may be switched off dynamically to save battery power as the ambient light source may not emit enough ambient light to measure the PPG signal. In cases where there is no ambient light, or very low level of ambient light, there may not be improvement from using ambient light cancellation.

For example, at night, the wearable device may measure the second PPG signal derived from the ambient light source. The wearable device may take initial measurements of ambient light to determine whether there is any or enough ambient light to measure the PPG signal. If the wearable device determines that there is little to no ambient light, the wearable device may deactivate the ambient light cancellation technique at 540. After deactivating the ambient light cancellation technique, the wearable device may periodically measure the second PPG signal derived from the ambient light source to determine whether to activate the ambient light cancellation technique. In some cases, after deactivating the ambient light cancellation technique, the wearable device may refrain from periodically measuring the second PPG signal derived from the ambient light source until the wearable device detects motion. In such cases, the wearable device may identify movement and measure the PPG signals derived from the LED and the ambient light source.

For example, at 540), the wearable device may identify movement of a user wearing the wearable device after deactivating the ambient light cancellation technique. The wearable device may identify that the user is waking up based on identifying the movement and determine whether to use ambient light or the LED as the light source. In such cases, the wearable device may measure the first PPG signal and the second PPG signal in response to identifying the movement by the user and to determine whether there is enough ambient light and the quality of the ambient light satisfies the threshold to use the ambient light as the source for PPG measurements.

The wearable device may use the motion of the wearable device to determine when the user wakes up. For example, the wearable device may perform periodic checks to determine if the amount of ambient light has changed and the ambient light cancellation technique may be turned back on. The periodic checks may be performed at varying intervals to determine whether the amount of ambient light has changed. For example, the periodic checks may be performed every 30 minutes, every hour, or every 2 hours. In some cases, the wearable device may use sleep timing data from the wearable device to predict when the user is likely to sleep, thus knowing when to switch off ambient light cancellation. The wearable device may use the calendar date, time of day, user location, or a combination thereof to determine sunrise and sunset to utilize the ambient light cancellation technique accordingly. For example, the wearable device may use a time for sunrise to predict an increase in ambient light levels.

At 530, the wearable device may adjust the power output level of the light source powered by the wearable device based on deactivating the ambient light cancellation technique. For example, the power output level of the light source powered by the wearable device may be adjusted to be less than a baseline power output level of the light source powered by the wearable device in response to determining that the quality metric of the second PPG signal fails to satisfy the threshold, the ambient light cancellation technique is deactivated, or both. In such cases, the wearable device may perform the PPG measurement using a low powered LED.

Figure 6:
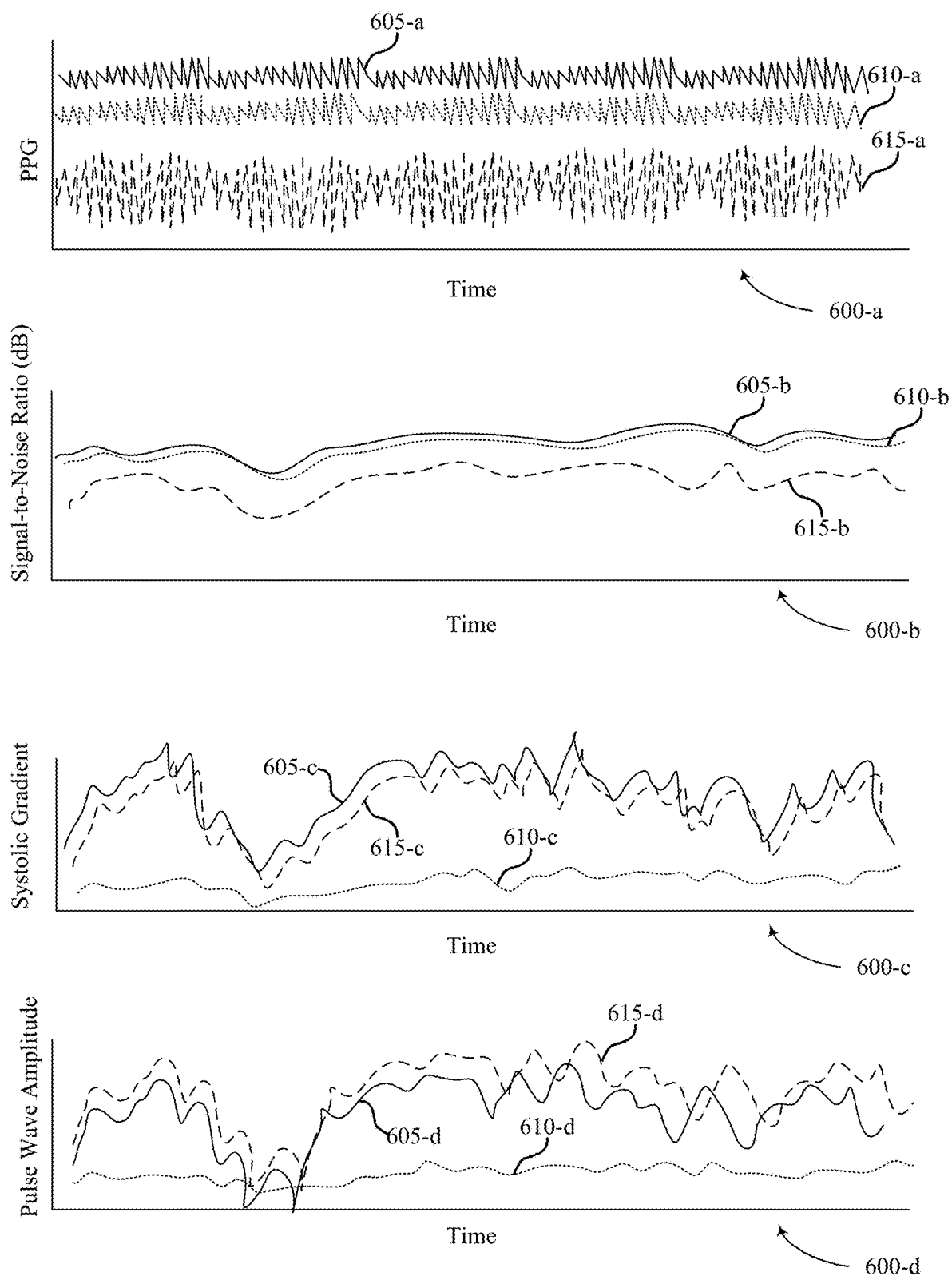
FIG. 6 shows an example of timing diagrams that supports low power optical measurements in accordance with aspects of the present disclosure.

FIG. 6 shows an example of timing diagrams 600 that supports low power optical measurements in accordance with aspects of the present disclosure. The timing diagrams 600 may implement, or be implemented by, aspects of the system 100, system 200, wearable device diagram 300, wearable device diagram 400, process flow 500, or a combination thereof.

The timing diagram 600-*a* may include a first PPG signal 605-*a*, a second PPG signal 610-*a*, and a third PPG signal 615-*a*. The first PPG signal 605-*a* may be an example of a PPG signal from a light source powered external to the wearable device (e.g., an ambient light source). The second PPG signal 610-*a* may be an example of a PPG signal from a first green LED and received at a first photodetector. The third PPG signal 615-*a* may be an example of a PPG signal from a second green LED and received at a second photodetector. In cases where a first green LED and a second green LED fire or activate simultaneously, the behavior of green light within a user's finger may be different due to physiological characteristics of the user's skin and other tissue, which may result in different arrival times of the green light at the respective photodetectors.

The timing diagram 600-*a* may illustrate an example of PPG signal comparison in which the first PPG signal 605-*a*, the second PPG signal 610-*a*, and the third PPG signal 615-*a* may be compared to each other. For example, the wearable device may compare a morphology of the first PPG signal 605-*a* and a morphology of the second PPG signal 610-*a*. The wearable device may compare the morphology of the first PPG signal 605-*a* and a morphology of the third PPG signal 615-*a*.

For example, the electrical current of the first PPG signal 605-*a* may be greater (e.g., higher) than the second PPG signal 610-*a* and the third PPG signal 615-*a*. The electrical current of the second PPG signal 610-*a* may be greater than the third PPG signal 615-*a*. The wearable device may calculate the quality metric of the first PPG signal 605-*a* associated with the ambient light source in response to comparing the morphology of the first PPG signal 605-*a* and the morphology of the second PPG signal 610-*a*, the third PPG signal 615-*a*, or both. The morphology of the first PPG signal 605-*a* may match (e.g., align) with the morphology of the second PPG signal 610-*a*. The morphology of the first PPG signal 605-*a* may be different from the morphology of the third PPG signal 615-*a*.

In such cases, the wearable device may determine that the quality metric of the first PPG signal 605-*a* may satisfy the threshold based on determining that the morphology of the first PPG signal 605-*a* aligns with the morphology of the second PPG signal 610-*a*. The wearable device may adjust the power outlet level of the first green LED associated with the second PPG signal 610-*a* and utilize the ambient light source to perform the PPG measurements in response to calculating the quality metric of the first PPG signal 605-*a*, comparing the morphologies, or both.

The morphology of the PPG signals may include a signal to noise ratio. The timing diagram 600-*b* may include a first PPG signal 605-*b*, a second PPG signal 610-*b*, and a third PPG signal 615-*b*, as described with reference to timing diagram 600-*a*. The timing diagram 600-*b* may illustrate an example of the signal to noise ratio of each PPG signal. For example, the wearable device may calculate the signal to noise ratio of the first PPG signal 605-*b*, the second PPG signal 610-*b*, and the third PPG signal 615-*b*.

The signal to noise ratio of the first PPG signal 605-*b* may be greater than the second PPG signal 610-*b* and the third PPG signal 615-*b*. The signal to noise ratio of the second PPG signal 610-*b* may be greater than the third PPG signal 615-*b*. The wearable device may calculate the quality metric of the first PPG signal 605-*b* associated with the ambient light source in response to calculating the signal to noise ratio of the first PPG signal 605-*b*. In some cases, the wearable device may calculate the quality metric of the second PPG signal 610-*b* and the third PPG signal 615-*b* in response to calculating the signal to noise ratio of the second PPG signal 610-*b* and the third PPG signal 615-*b*, respectively.

The ambient light source (e.g., the first PPG signal 605-*b*) may include the highest signal to noise ratio due to the least amount of electronic noise being present, the external noise is less attenuated and/or amplified, or both. In some cases, a dynamic range of measurements may change in different portions of the wearable device. For example, the external noise may be more attenuated and/or amplified in different portions of the wearable device where the photodetectors, the LEDs, or both are located. In such cases, when measuring with an asymmetrical PPG multichannel system, the wearable device may choose the optimal channel to perform the PPG measurements to lower the power consumption of the wearable device and maintain signal quality of the PPG measurements.

The morphology of the signal to noise ratio of the first PPG signal 605-*b* may match (e.g., align) with the morphology of the signal to noise ratio of the second PPG signal 610-*b*. The morphology of the signal to noise ratio of the first PPG signal 605-*b* may be different from the signal to noise ratio of the third PPG signal 615-*b*. For example, the morphology of the signal to noise ratio of the first PPG signal 605-*b* does not align with the morphology of the signal to noise ratio of the third PPG signal 615-*b*.

The wearable device may determine that the quality metric of the first PPG signal 605-*b* satisfies the threshold based on calculating the signal to noise ratio of the first PPG signal 605-*b*. The wearable device may adjust the power outlet level of the first green LED associated with the second PPG signal 610-*b* and utilize the ambient light source associated with the first PPG signal 605-*b* to perform the PPG measurements. For example, the wearable device may adjust the power output level of the first green LED in response to calculating the quality metric of the first PPG signal 605-*b*, calculating the signal to noise ratio of the first PPG signal 605-*b*, calculating the signal to noise ratio of the second PPG signal 610-*b*, calculating the signal to noise ratio of the third PPG signal 615-*b*, or a combination thereof. In such cases, the wearable device may determine the quality metric of the signal to noise ratio to determine whether to use the light source as ambient light or the LEDs.

In some cases, the morphology of the PPG signals may include systolic gradient. Systolic gradient may be an example of a steepness of the rising edge of each pulse wave. As described with reference to the signal to noise ratio calculations of timing diagram 600-*b*, the wearable device may calculate the systolic gradient of the first PPG signal 605-*c*, the second PPG signal 610-*c*, and the third PPG signal 615-*c*.

For example, the wearable device may determine that the systolic gradient of the first PPG signal 605-*c* is greater than the third PPG signal 615-*c* and the second PPG signal 610-*c*. The wearable device may determine that the systolic gradient of the first PPG signal 605-*c* is greater than the second PPG signal 610-*c*. In such case, the wearable device may determine that the morphology of the systolic gradient of the first PPG signal 605-*c* aligns with the systolic gradient of the third PPG signal 615-*c*, and the wearable device may determine that the systolic gradient of the first PPG signal 605-*c* may be different than the systolic gradient of the second PPG signal 610-*c*. For example, the wearable device may determine that the systolic gradient of the first PPG signal 605-*c* is greater than the systolic gradient of the second PPG signal 610-*c*.

The wearable device may adjust the power outlet level of the second green LED associated with the third PPG signal 615-*c* and utilize the ambient light source to perform the PPG measurements in response to calculating the systolic gradient. For example, the wearable device may adjust the power output level of the second green LED in response to calculating the quality metric (e.g., the systolic gradient) of the first PPG signal 605-*c*, the second PPG signal 610-*c*, the third PPG signal 615-*c*, or a combination thereof.

The morphology of the PPG signals may include a pulse wave amplitude. The pulse amplitude may be an example of a difference between a maximum of the PPG pulse waveform and a minimum of the PPG pulse waveform. The wearable device may calculate the pulse wave amplitude of the first PPG signal 605-*d*, the second PPG signal 610-*d*, and the third PPG signal 615-*d*, as described with reference to the timing diagrams 600.

Based on the calculations, the pulse wave amplitude of the third PPG signal 615-*d* may be determined to be greater than the first PPG signal 605-*d* and the second PPG signal 610-*d*. For example, the wearable device may determine that the pulse wave amplitude of the first PPG signal 605-*d* is greater than the second PPG signal 610-*d*. The wearable device may determine that the pulse wave amplitude of the first PPG signal 605-*d* is similar to the third PPG signal 615-*d*. For example, the wearable device may determine that morphology of the pulse wave amplitude of the first PPG signal 605-*d* may match with the pulse wave amplitude of the third PPG signal 615-*d*, and that the morphology of the pulse wave amplitude of the first PPG signal 605-*d* is different than the pulse wave amplitude of the second PPG signal 610-*d*.

In response to calculating the pulse wave amplitudes of the respective PPG signals, the wearable device may adjust the power outlet level of the second green LED associated with the third PPG signal 615-*d* and utilize the ambient light source to perform the PPG measurements. For example, the wearable device may adjust the power output level of the second green LED in response to calculating the quality metric (e.g., the pulse wave amplitude) of the first PPG signal 605-*d*, the second PPG signal 610-*d*, the third PPG signal 615-*d*, or a combination thereof.

For example, the wearable device may analyze the pulse wave amplitude of the PPG signals and optimize the LED current based on the pulse wave amplitudes. In some cases, the wearable device may increase the LED current if the pulse wave amplitude is too low. For example, the current of the LED associated with the second PPG signal 610-*d* may be increased. In some cases, a pulsating source may be located closest to the third PPG signal 615-*d*. In such cases, the third PPG signal 615-*d* may include the greatest pulse wave amplitude. The ambient light source may include a pulse wave amplitude similar to the pulse wave amplitude of the second green LED due to the least amount of electronic noise being present, the external noise is less attenuated and/or amplified, or both.

Figure 7:
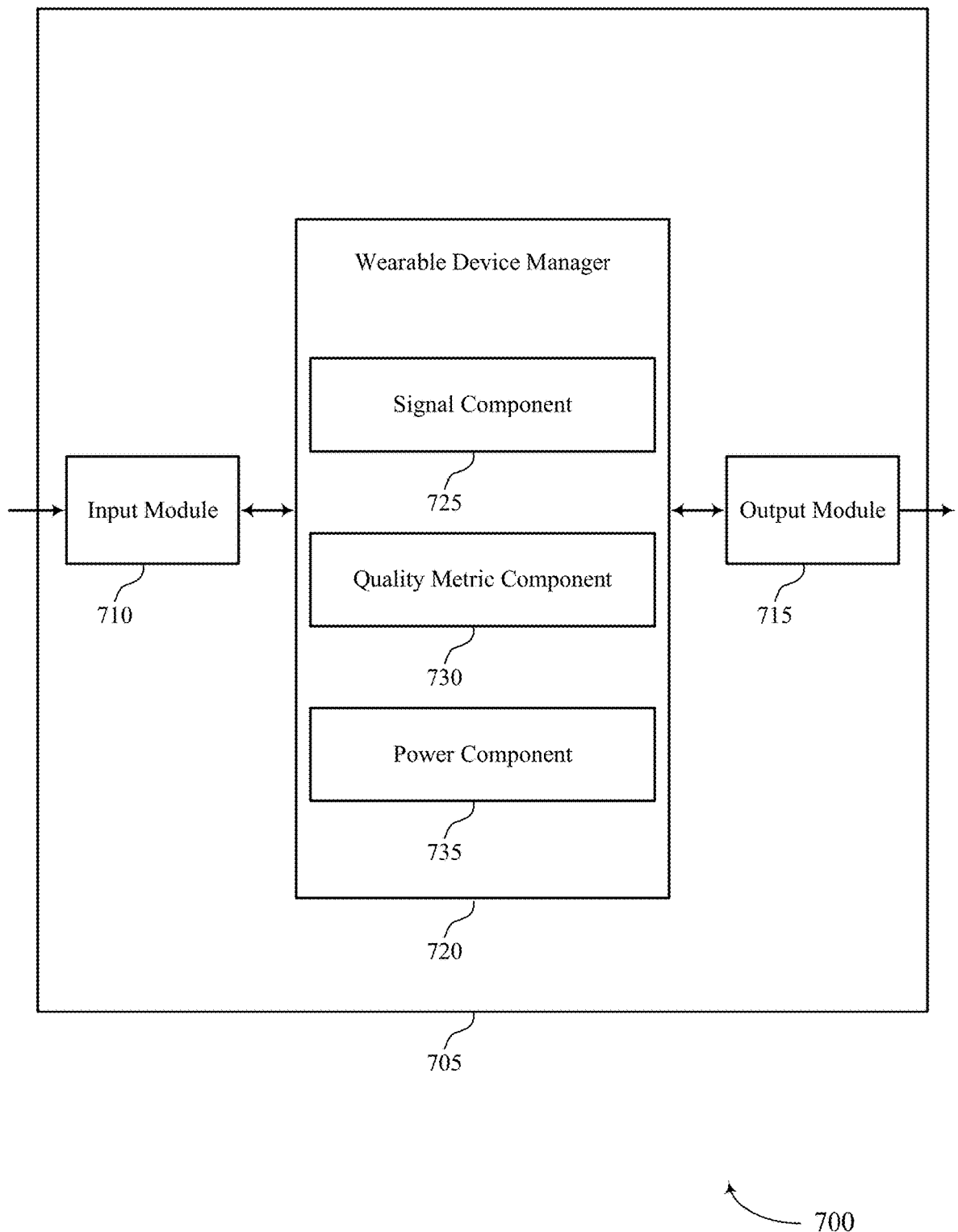
FIG. 7 shows a block diagram of an apparatus that supports low power optical measurements in accordance with aspects of the present disclosure.

FIG. 7 shows a block diagram 700 of a device 705 that supports low power optical measurements in accordance with aspects of the present disclosure. The device 705 may include an input module 710, an output module 715, and a wearable device manager 720. The device 705 may also include a processor. Each of these components may be in communication with one another (e.g., via one or more buses).

For example, the wearable device manager 720 may include a signal component 725, a quality metric component 730, a power component 735, or any combination thereof. In some examples, the wearable device manager 720, or various components thereof, may be configured to perform various operations (e.g., receiving, monitoring, transmitting) using or otherwise in cooperation with the input module 710, the output module 715, or both. For example, the wearable device manager 720 may receive information from the input module 710, send information to the output module 715, or be integrated in combination with the input module 710, the output module 715, or both to receive information, transmit information, or perform various other operations as described herein.

The signal component 725 may be configured as or otherwise support a means for measuring, at a photodetector on the wearable device, a first photoplethysmography (PPG) signal derived from an ambient light source that is powered externally to the wearable device. The quality metric component 730 may be configured as or otherwise support a means for calculating, by the wearable device, a quality metric of the first PPG signal based at least in part on measuring the first PPG signal. The power component 735 may be configured as or otherwise support a means for adjusting, by the wearable device, the power output level of the light source powered by the wearable device based at least in part on the quality metric of the first PPG signal.

Figure 8:
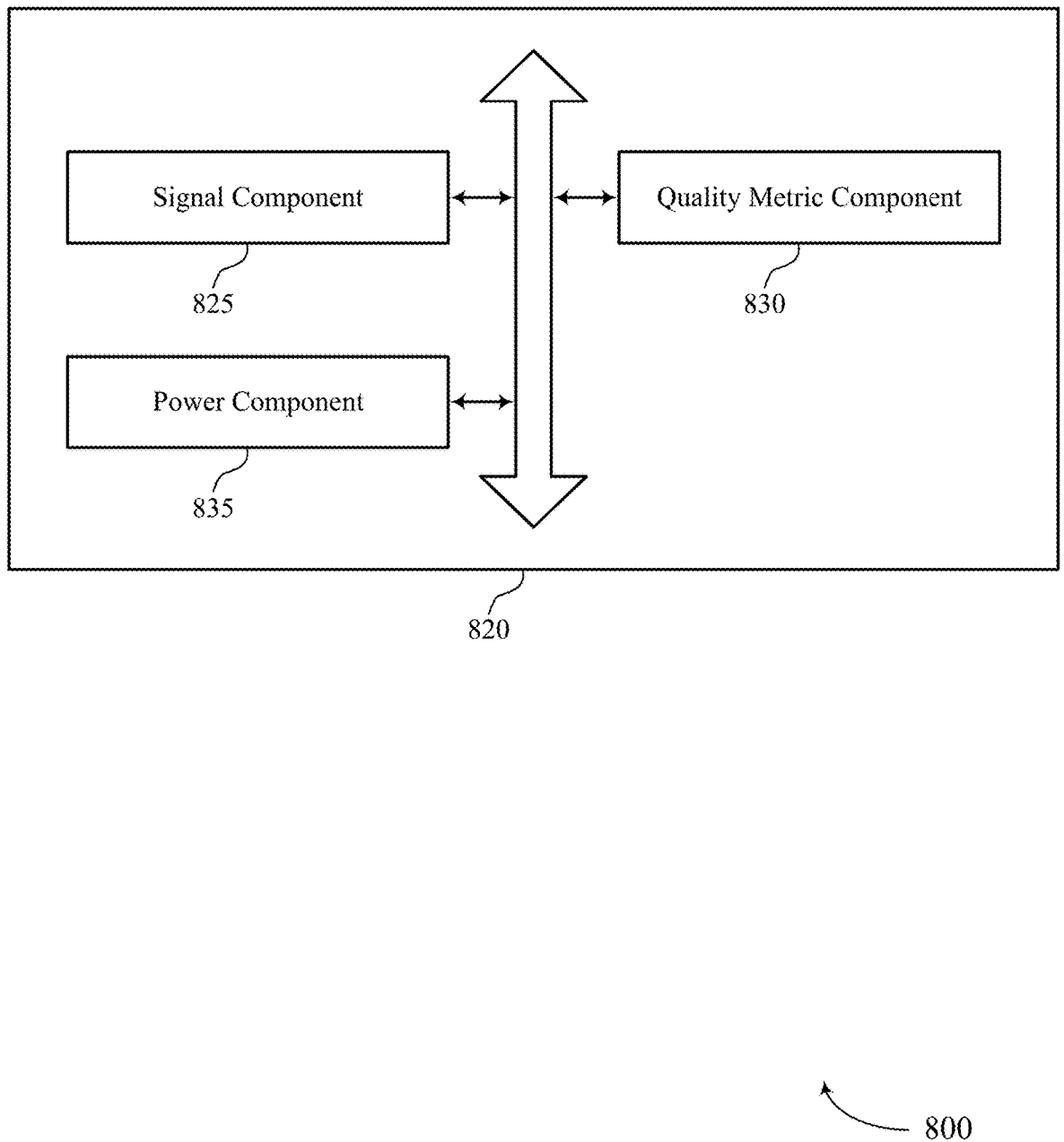
FIG. 8 shows a block diagram of a wearable device manager that supports low power optical measurements in accordance with aspects of the present disclosure.

FIG. 8 shows a block diagram 800 of a wearable device manager 820 that supports low power optical measurements in accordance with aspects of the present disclosure. The wearable device manager 820 may be an example of aspects of a wearable device manager or a wearable device manager 720, or both, as described herein. The wearable device manager 820, or various components thereof, may be an example of means for performing various aspects of low power optical measurements as described herein. For example, the wearable device manager 820 may include a signal component 825, a quality metric component 830, a power component 835, or any combination thereof. Each of these components may communicate, directly or indirectly, with one another (e.g., via one or more buses).

The signal component 825 may be configured as or otherwise support a means for measuring, at a photodetector on the wearable device, a first photoplethysmography (PPG) signal derived from an ambient light source that is powered externally to the wearable device. The quality metric component 830 may be configured as or otherwise support a means for calculating, by the wearable device, a quality metric of the first PPG signal based at least in part on measuring the first PPG signal. The power component 835 may be configured as or otherwise support a means for adjusting, by the wearable device, the power output level of the light source powered by the wearable device based at least in part on the quality metric of the first PPG signal.

In some examples, the quality metric component 830 may be configured as or otherwise support a means for measuring, at the photodetector on the wearable device, a second PPG signal derived from the light source powered by the wearable device and comparing, by the wearable device, a morphology of the first PPG signal and a morphology of the second PPG signal based at least in part on measuring the first PPG signal, wherein calculating the quality metric is based at least in part on comparing the morphology of the first PPG signal and the morphology of the second PPG signal, wherein the morphology of the first PPG signal and the morphology of the second PPG signal each comprise a pulse amplitude, a systolic gradient, a signal to noise ratio, or a combination thereof.

In some examples, to support calculating the quality metric, the signal component 825 may be configured as or otherwise support a means for calculating a pulse amplitude of the first PPG signal based at least in part on measuring the first PPG signal, wherein adjusting the power output level is based at least in part on calculating the pulse amplitude of the first PPG signal.

In some examples, to support calculating the quality metric, the signal component 825 may be configured as or otherwise support a means for calculating a signal to noise ratio of the first PPG signal based at least in part on measuring the first PPG signal, wherein adjusting the power output level is based at least in part on calculating the signal to noise ratio of the first PPG signal.

In some examples, to support calculating the quality metric, the signal component 825 may be configured as or otherwise support a means for calculating a systolic gradient of the first PPG signal based at least in part on measuring the first PPG signal, wherein adjusting the power output level is based at least in part on calculating the systolic gradient of the first PPG signal.

In some examples, the quality metric component 830 may be configured as or otherwise support a means for determining that the quality metric of the first PPG signal satisfies a threshold based at least in part on calculating the quality metric. In some examples, the power component 840 may be configured as or otherwise support a means for deactivating an ambient light cancellation technique based at least in part on determining that the quality metric satisfies the threshold.

In some examples, the power component 835 may be configured as or otherwise support a means for deactivating the light source powered by the wearable device based at least in part on determining that the quality metric satisfies the threshold, wherein adjusting the power output level is based at least in part on deactivating the light source powered by the wearable device.

In some examples, the quality metric component 830 may be configured as or otherwise support a means for determining that the quality metric associated with the first PPG signal fails to satisfy a threshold based at least in part on calculating the quality metric. In some examples, the power component 835 may be configured as or otherwise support a means for activating an ambient light cancellation technique based at least in part on determining that the quality metric fails to satisfy the threshold.

In some examples, the quality metric component 830 may be configured as or otherwise support a means for determining that the quality metric associated with the first PPG signal fails to satisfy a threshold based at least in part on calculating the quality metric. In some examples, the power component 835 may be configured as or otherwise support a means for deactivating an ambient light cancellation technique based at least in part on determining that the quality metric fails to satisfy the threshold.

In some examples, the signal component 825 may be configured as or otherwise support a means for identifying movement of a user wearing the wearable device after deactivating the ambient light cancellation technique, wherein measuring the first PPG signal is based at least in part on identifying the movement by the user.

In some examples, the power output level of the light source powered by the wearable device is adjusted to be less than a baseline power output level of the light source powered by the wearable device.

Figure 9:
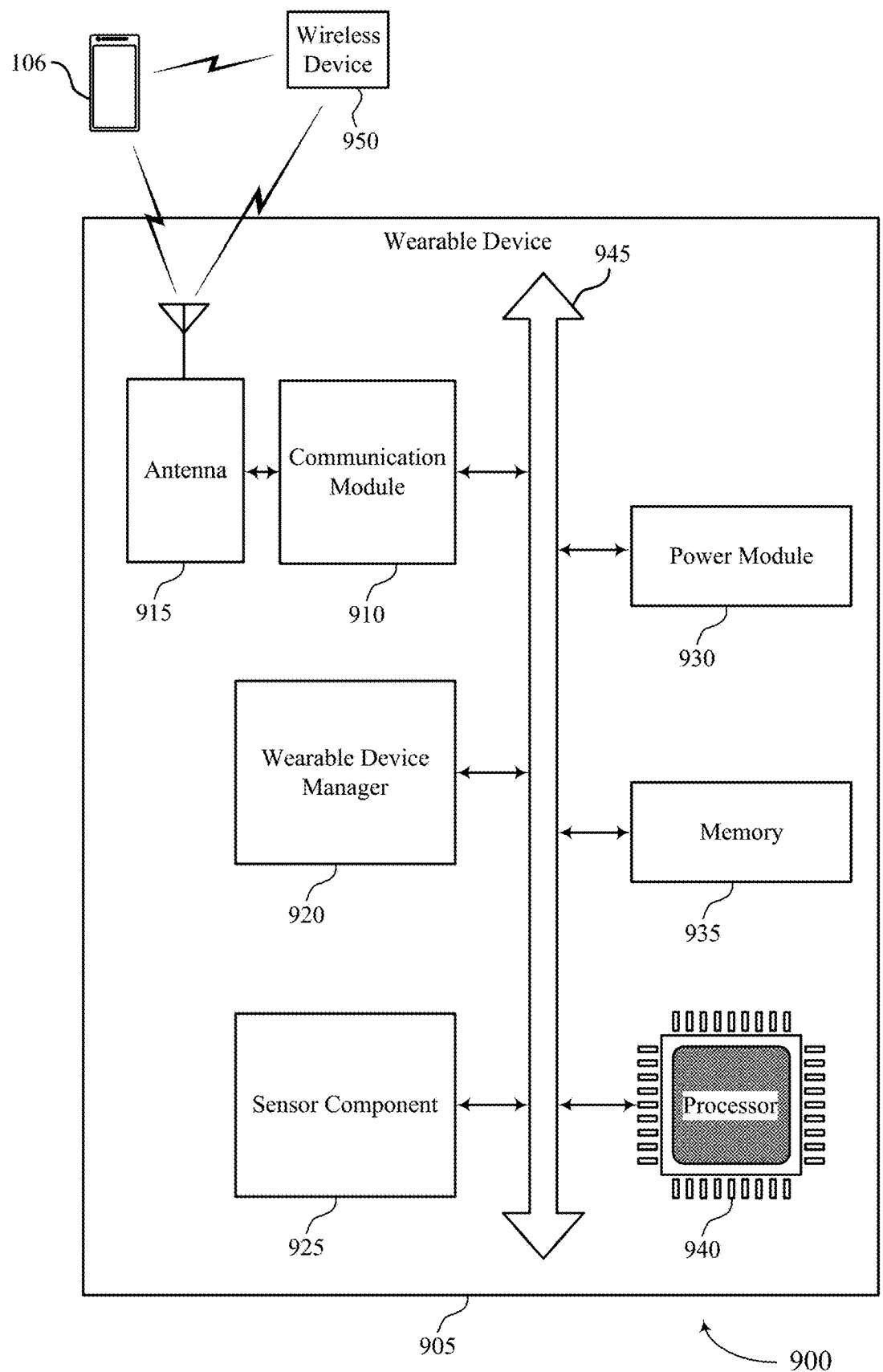
FIG. 9 shows a diagram of a system including a device that supports low power optical measurements in accordance with aspects of the present disclosure.

FIG. 9 shows a diagram of a system 900 including a device 905 that supports low power optical measurements in accordance with aspects of the present disclosure. The device 905 may be an example of or include the components of a device 705 as described herein. The device 905 may include an example of a wearable device 104, as described previously herein. The device 905 may include components for bi-directional communications including components for transmitting and receiving communications with a user device 106 and a server 110, such as a wearable device manager 920, a communication module 910, an antenna 915, a sensor component 925, a power module 930, a memory 935, a processor 940, and a wireless device 950. These components may be in electronic communication or otherwise coupled (e.g., operatively, communicatively, functionally, electronically, electrically) via one or more buses (e.g., a bus 945).

For example, the wearable device manager 920 may be configured as or otherwise support a means for measuring, at a photodetector on the wearable device, a first photoplethysmography (PPG) signal derived from an ambient light source that is powered externally to the wearable device. The wearable device manager 920 may be configured as or otherwise support a means for calculating, by the wearable device, a quality metric of the first PPG signal based at least in part on measuring the first PPG signal. The wearable device manager 920 may be configured as or otherwise support a means for adjusting, by the wearable device, the power output level of the light source powering by the wearable device based at least in part on the quality metric of the first PPG signal.

By including or configuring the wearable device manager 920 in accordance with examples as described herein, the device 905 may support techniques improved communication reliability, reduced latency, improved user experience related to reduced processing, reduced power consumption, more efficient utilization of communication resources, improved coordination between devices, longer battery life, improved utilization of processing capability, and the like.

Figure 10:
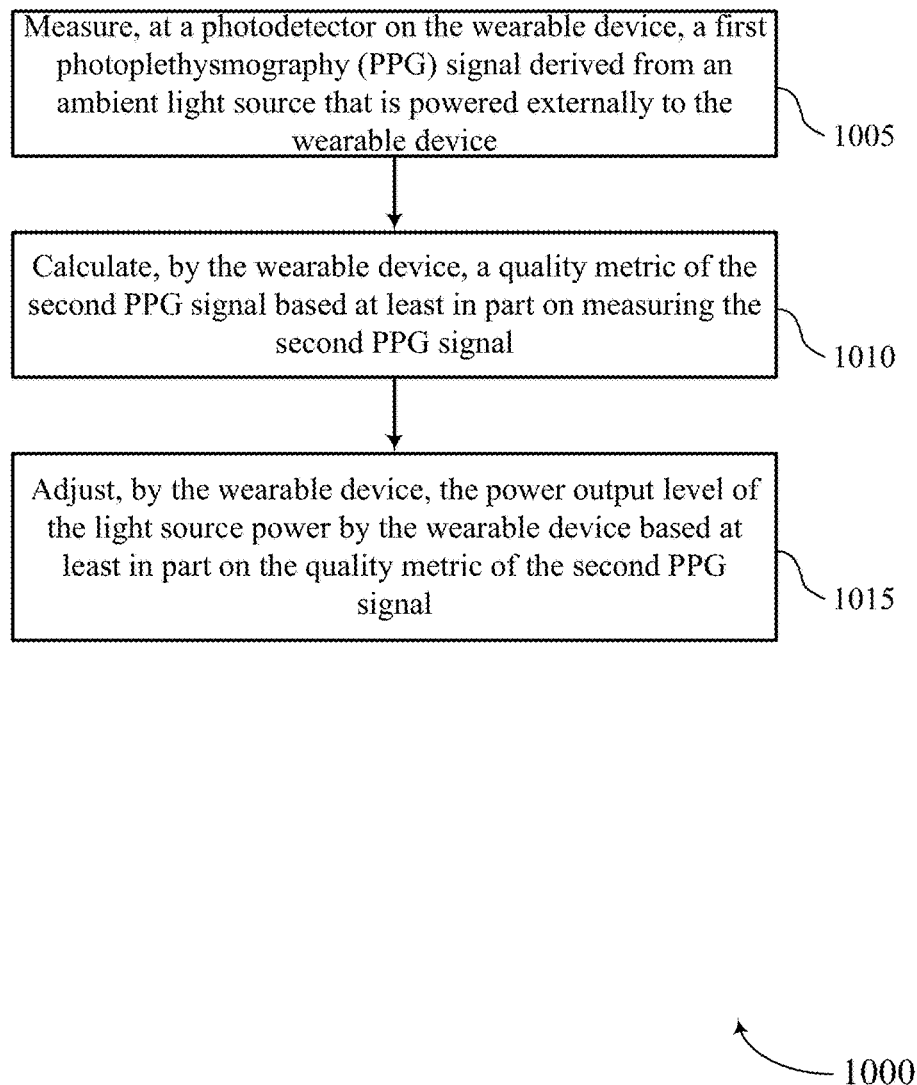
FIGS. 10 and 11 show flowcharts illustrating methods that support low power optical measurements in accordance with aspects of the present disclosure.

FIG. 10 shows a flowchart illustrating a method 1000 that supports low power optical measurements in accordance with aspects of the present disclosure. The operations of the method 1000 may be implemented by a wearable device or its components as described herein. For example, the operations of the method 1000 may be performed by a wearable device as described with reference to FIGS. 1 through 9. In some examples, a wearable device may execute a set of instructions to control the functional elements of the wearable device to perform the described functions. Additionally, or alternatively, the wearable device may perform aspects of the described functions using special-purpose hardware.

At 1005, the method may include measuring, at a photodetector on the wearable device, a first photoplethysmography (PPG) signal derived from an ambient light source that is powered externally to the wearable device. The operations of block 1005 may be performed in accordance with examples as disclosed herein. In some examples, aspects of the operations of 1005 may be performed by a signal component 825 as described with reference to FIG. 8.

At 1010, the method may include calculating, by the wearable device, a quality metric of the first PPG signal based at least in part on measuring the first PPG signal. The operations of block 1010 may be performed in accordance with examples as disclosed herein. In some examples, aspects of the operations of 1010 may be performed by a quality metric component 830 as described with reference to FIG. 8.

At 1015, the method may include adjusting, by the wearable device, the power output level of the light source powered by the wearable device based at least in part on the quality metric of the first PPG signal. The operations of block 1015 may be performed in accordance with examples as disclosed herein. In some examples, aspects of the operations of 1015 may be performed by a power component 835 as described with reference to FIG. 8.

Figure 11:
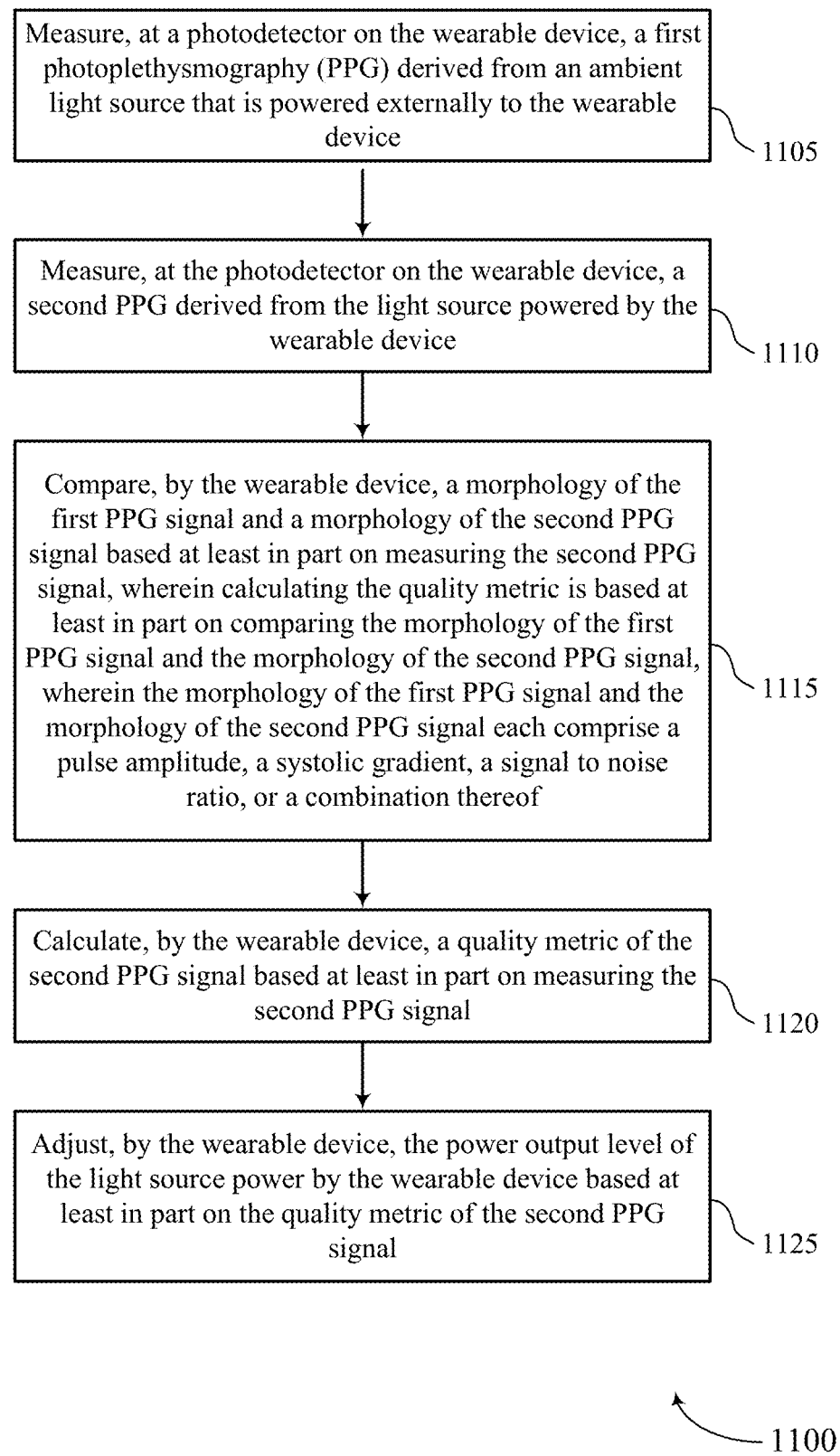

FIG. 11 shows a flowchart illustrating a method 1100 that supports low power optical measurements in accordance with aspects of the present disclosure. The operations of the method 1100 may be implemented by a wearable device or its components as described herein. For example, the operations of the method 1100 may be performed by a wearable device as described with reference to FIGS. 1 through 9. In some examples, a wearable device may execute a set of instructions to control the functional elements of the wearable device to perform the described functions. Additionally, or alternatively, the wearable device may perform aspects of the described functions using special-purpose hardware.

At 1105, the method may include measuring, at a photodetector on the wearable device, a first photoplethysmography (PPG) signal derived from an ambient light source that is powered externally to the wearable device. The operations of block 1105 may be performed in accordance with examples as disclosed herein. In some examples, aspects of the operations of 1105 may be performed by a signal component 825 as described with reference to FIG. 8.

At 1110, the method may include measuring, at the photodetector on the wearable device, a second PPG signal derived from the light source powered by the wearable device. The operations of block 1110 may be performed in accordance with examples as disclosed herein. In some examples, aspects of the operations of 1110 may be performed by a quality metric component 830 as described with reference to FIG. 8.

At 1115, the method may include comparing, by the wearable device, a morphology of the first PPG signal and a morphology of the second PPG signal based at least in part on measuring the first PPG signal, wherein calculating the quality metric is based at least in part on comparing the morphology of the first PPG signal and the morphology of the second PPG signal, wherein the morphology of the first PPG signal and the morphology of the second PPG signal each comprise a pulse amplitude, a systolic gradient, a signal to noise ratio, or a combination thereof. The operations of block 1115 may be performed in accordance with examples as disclosed herein. In some examples, aspects of the operations of 1115 may be performed by a quality metric component 830 as described with reference to FIG. 8.

At 1120, the method may include calculating, by the wearable device, a quality metric of the first PPG signal based at least in part on measuring the first PPG signal. The operations of block 1120 may be performed in accordance with examples as disclosed herein. In some examples, aspects of the operations of 1120 may be performed by a quality metric component 830 as described with reference to FIG. 8.

At 1125, the method may include adjusting, by the wearable device, the power output level of the light source powered by the wearable device based at least in part on the quality metric of the first PPG signal. The operations of block 1125 may be performed in accordance with examples as disclosed herein. In some examples, aspects of the operations of 1125 may be performed by a power component 835 as described with reference to FIG. 8.

It should be noted that the methods described above describe possible implementations, and that the operations and the steps may be rearranged or otherwise modified and that other implementations are possible. Furthermore, aspects from two or more of the methods may be combined.

A method is described. The method may include measuring, at a photodetector on the wearable device, a first PPG signal derived from an ambient light source that is powered externally to the wearable device, calculating, by the wearable device, a quality metric of the first PPG signal based at least in part on measuring the first PPG signal, and adjusting, by the wearable device, the power output level of the light source powered by the wearable device based at least in part on the quality metric of the first PPG signal.

An apparatus is described. The apparatus may include a processor, memory coupled with the processor, and instructions stored in the memory. The instructions may be executable by the processor to cause the apparatus to measure, at a photodetector on the wearable device, a first PPG signal derived from an ambient light source that is powered externally to the wearable device, calculate, by the wearable device, a quality metric of the first PPG signal based at least in part on measuring the first PPG signal, and adjusting, by the wearable device, the power output level of the light source power by the wearable device based at least in part on the quality metric of the first PPG signal.

Another apparatus is described. The apparatus may include means for measuring, at a photodetector on the wearable device, a first PPG signal derived from an ambient light source that is powered externally to the wearable device, means for calculating, by the wearable device, a quality metric of the first PPG signal based at least in part on measuring the first PPG signal, and means for adjusting, by the wearable device, the power output level of the light source powered by the wearable device based at least in part on the quality metric of the first PPG signal.

A non-transitory computer-readable medium storing code is described. The code may include instructions executable by a processor to measure, at a photodetector on the wearable device, a first PPG signal derived from an ambient light source that is powered externally to the wearable device, calculate, by the wearable device, a quality metric of the first PPG signal based at least in part on measuring the first PPG signal, and adjusting, by the wearable device, the power output level of the light source power by the wearable device based at least in part on the quality metric of the first PPG signal.

Some examples of the method, apparatuses, and non-transitory computer-readable medium described herein may further include operations, features, means, or instructions for measuring, at the photodetector on the wearable device, a second PPG signal derived from the light source powered by the wearable device and comparing, by the wearable device, a morphology of the first PPG signal and a morphology of the second PPG signal based at least in part on measuring the first PPG signal, wherein calculating the quality metric may be based at least in part on comparing the morphology of the first PPG signal and the morphology of the second PPG signal, wherein the morphology of the first PPG signal and the morphology of the second PPG signal each comprise a pulse amplitude, a systolic gradient, a signal to noise ratio, or a combination thereof.

In some examples of the method, apparatuses, and non-transitory computer-readable medium described herein, calculating the quality metric may include operations, features, means, or instructions for calculating a pulse amplitude of the first PPG signal based at least in part on measuring the first PPG signal, wherein adjusting the power output level may be based at least in part on calculating the pulse amplitude of the first PPG signal.

In some examples of the method, apparatuses, and non-transitory computer-readable medium described herein, calculating the quality metric may include operations, features, means, or instructions for calculating a signal to noise ratio of the first PPG signal based at least in part on measuring the first PPG signal, wherein adjusting the power output level may be based at least in part on calculating the signal to noise ratio of the first PPG signal.

In some examples of the method, apparatuses, and non-transitory computer-readable medium described herein, calculating the quality metric may include operations, features, means, or instructions for calculating a systolic gradient of the first PPG signal based at least in part on measuring the first PPG signal, wherein adjusting the power output level may be based at least in part on calculating the systolic gradient of the first PPG signal.

Some examples of the method, apparatuses, and non-transitory computer-readable medium described herein may further include operations, features, means, or instructions for determining that the quality metric of the first PPG signal satisfies a threshold based at least in part on calculating the quality metric and deactivating an ambient light cancellation technique based at least in part on determining that the quality metric satisfies the threshold.

Some examples of the method, apparatuses, and non-transitory computer-readable medium described herein may further include operations, features, means, or instructions for deactivating the light source powered by the wearable device based at least in part on determining that the quality metric satisfies the threshold, wherein adjusting the power output level may be based at least in part on deactivating the light source powered by the wearable device.

Some examples of the method, apparatuses, and non-transitory computer-readable medium described herein may further include operations, features, means, or instructions for determining that the quality metric associated with the first PPG signal fails to satisfy a threshold based at least in part on calculating the quality metric and activating an ambient light cancellation technique based at least in part on determining that the quality metric fails to satisfy the threshold.

Some examples of the method, apparatuses, and non-transitory computer-readable medium described herein may further include operations, features, means, or instructions for determining that the quality metric associated with the first PPG signal fails to satisfy a threshold based at least in part on calculating the quality metric and deactivating an ambient light cancellation technique based at least in part on determining that the quality metric fails to satisfy the threshold.

Some examples of the method, apparatuses, and non-transitory computer-readable medium described herein may further include operations, features, means, or instructions for identifying movement of a user wearing the wearable device after deactivating the ambient light cancellation technique, wherein measuring the first PPG signal may be based at least in part on identifying the movement by the user.

In some examples of the method, apparatuses, and non-transitory computer-readable medium described herein, the power output level of the light source powered by the wearable device may be adjusted to be less than a baseline power output level of the light source powered by the wearable device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method of adjusting a power output level of a light source on a wearable device, comprising:
    measuring, at a photodetector on the wearable device, a first photoplethysmography (PPG) signal derived from an ambient light source that is powered externally to the wearable device;
    identifying one or more features of a morphology of the first PPG signal derived from the ambient light source based at least in part on measuring the first PPG signal, wherein the one or more features of the morphology comprises a pulse amplitude, a systolic gradient, a signal to noise ratio, or a combination thereof;
    calculating, by the wearable device, a quality metric of the first PPG signal based at least in part on the one or more features of the morphology of the first PPG signal; and
    adjusting, by the wearable device, the power output level of the light source powered by the wearable device based at least in part on the quality metric of the first PPG signal.

2. The method of claim 1, further comprising:
    measuring, at the photodetector on the wearable device, a second PPG signal derived from the light source powered by the wearable device; and
    comparing, by the wearable device, the morphology of the first PPG signal and a morphology of the second PPG signal based at least in part on measuring the first PPG signal, wherein calculating the quality metric is based at least in part on comparing the morphology of the first PPG signal and the morphology of the second PPG signal, the morphology of the second PPG signal comprises a pulse amplitude, a systolic gradient, a signal to noise ratio, or a combination thereof.

3. The method of claim 1, wherein calculating the quality metric further comprises:
    calculating the pulse amplitude of the first PPG signal based at least in part on measuring the first PPG signal, wherein adjusting the power output level is based at least in part on calculating the pulse amplitude of the first PPG signal.

4. The method of claim 1, wherein calculating the quality metric further comprises:
    calculating the signal to noise ratio of the first PPG signal based at least in part on measuring the first PPG signal, wherein adjusting the power output level is based at least in part on calculating the signal to noise ratio of the first PPG signal.

5. The method of claim 1, wherein calculating the quality metric further comprises:
    calculating the systolic gradient of the first PPG signal based at least in part on measuring the first PPG signal, wherein adjusting the power output level is based at least in part on calculating the systolic gradient of the first PPG signal.

6. The method of claim 1, further comprising:
    determining that the quality metric of the first PPG signal satisfies a threshold based at least in part on calculating the quality metric; and
    deactivating an ambient light cancellation technique based at least in part on determining that the quality metric satisfies the threshold.

7. The method of claim 6, further comprising:
    deactivating the light source powered by the wearable device based at least in part on determining that the quality metric satisfies the threshold, wherein adjusting the power output level is based at least in part on deactivating the light source powered by the wearable device.

8. The method of claim 1, further comprising:
    determining that the quality metric associated with the first PPG signal fails to satisfy a threshold based at least in part on calculating the quality metric; and
    activating an ambient light cancellation technique based at least in part on determining that the quality metric fails to satisfy the threshold.

9. The method of claim 1, further comprising:
    determining that the quality metric associated with the first PPG signal fails to satisfy a threshold based at least in part on calculating the quality metric; and
    deactivating an ambient light cancellation technique based at least in part on determining that the quality metric fails to satisfy the threshold.

10. The method of claim 9, further comprising:
    identifying movement of a user wearing the wearable device after deactivating the ambient light cancellation technique, wherein measuring the first PPG signal is based at least in part on identifying the movement by the user.

11. The method of claim 1, wherein the power output level of the light source powered by the wearable device is adjusted to be less than a baseline power output level of the light source powered by the wearable device.

12. An apparatus, comprising:
a processor;
memory coupled with the processor; and
instructions stored in the memory and executable by the processor to cause the apparatus to:
measure, at a photodetector on a wearable device, a first photoplethysmography (PPG) signal derived from an ambient light source that is powered externally to the wearable device;
identify one or more features of a morphology of the first PPG signal derived from the ambient light source based at least in part on measuring the first PPG signal, wherein the one or more features of the morphology comprises a pulse amplitude, a systolic gradient, a signal to noise ratio, or a combination thereof;
calculate, by the wearable device, a quality metric of the first PPG signal based at least in part on the one or more features of the morphology of the first PPG signal; and
adjust, by the wearable device, a power output level of a light source powered by the wearable device based at least in part on the quality metric of the first PPG signal.

13. The apparatus of claim 12, wherein the instructions are further executable by the processor to cause the apparatus to:
measure, at the photodetector on a wearable device, a second PPG signal derived from a light source powered by the wearable device; and
compare, by the wearable device, the morphology of the first PPG signal and a morphology of the second PPG signal based at least in part on measuring the first PPG signal, wherein calculating the quality metric is based at least in part on comparing the morphology of the first PPG signal and the morphology of the second PPG signal, the morphology of the second PPG signal comprises a pulse amplitude, a systolic gradient, a signal to noise ratio, or a combination thereof.

14. The apparatus of claim 12, wherein the instructions to calculate the quality metric are further executable by the processor to cause the apparatus to:
calculate the pulse amplitude of the first PPG signal based at least in part on measuring the first PPG signal, wherein adjusting the power output level is based at least in part on calculating the pulse amplitude of the first PPG signal.

15. The apparatus of claim 12, wherein the instructions to calculate the quality metric are further executable by the processor to cause the apparatus to:
calculate the signal to noise ratio of the first PPG signal based at least in part on measuring the first PPG signal, wherein adjusting the power output level is based at least in part on calculating the signal to noise ratio of the first PPG signal.

16. The apparatus of claim 12, wherein the instructions to calculate the quality metric are further executable by the processor to cause the apparatus to:

calculate the systolic gradient of the first PPG signal based at least in part on measuring the first PPG signal, wherein adjusting the power output level is based at least in part on calculating the systolic gradient of the first PPG signal.

17. A non-transitory computer-readable medium storing code, the code comprising instructions executable by a processor to:
measure, at a photodetector on a wearable device, a first photoplethysmography (PPG) signal derived from an ambient light source that is powered externally to the wearable device;
identify one or more features of a morphology of the first PPG signal derived from the ambient light source based at least in part on measuring the first PPG signal, wherein the one or more features of the morphology comprises a pulse amplitude, a systolic gradient, a signal to noise ratio, or a combination thereof;
calculate, by the wearable device, a quality metric of the first PPG signal based at least in part on the one or more features of the morphology of the first PPG signal; and
adjust, by the wearable device, a power output level of the light source powered by the wearable device based at least in part on the quality metric of the first PPG signal.

18. The non-transitory computer-readable medium of claim 17, wherein the instructions are further executable by the processor to:
measure, at the photodetector on the wearable device, a second PPG signal derived from a light source powered by the wearable device; and
compare, by the wearable device, the morphology of the first PPG signal and a morphology of the second PPG signal based at least in part on measuring the first PPG signal, wherein calculating the quality metric is based at least in part on comparing the morphology of the first PPG signal and the morphology of the second PPG signal, the morphology of the second PPG signal comprises a pulse amplitude, a systolic gradient, a signal to noise ratio, or a combination thereof.

19. The non-transitory computer-readable medium of claim 17, wherein the instructions to calculate the quality metric are further executable by the processor to:
calculate the pulse amplitude of the first PPG signal based at least in part on measuring the first PPG signal, wherein adjusting the power output level is based at least in part on calculating the pulse amplitude of the first PPG signal.

20. The non-transitory computer-readable medium of claim 17, wherein the instructions to calculate the quality metric are further executable by the processor to:
calculate the signal to noise ratio of the first PPG signal based at least in part on measuring the first PPG signal, wherein adjusting the power output level is based at least in part on calculating the signal to noise ratio of the first PPG signal.

* * * * *